US010869690B2

(12) United States Patent
Parihar et al.

(10) Patent No.: US 10,869,690 B2
(45) Date of Patent: Dec. 22, 2020

(54) TROCAR OBTURATOR WITH TRANSVERSE NEEDLE PORTS

(71) Applicant: ETHICON LLC, Guaynabo, PR (US)

(72) Inventors: Shailendra K. Parihar, Mason, OH (US); Frederick E. Shelton, IV, Hillsboro, OH (US); Jason L. Harris, Lebanon, OH (US); Brian D. Schings, Cincinnati, OH (US); Michael A. Murray, Bellevue, KY (US); Melinda J. Tellmann, Franklin, OH (US); Devanathan Raghavan, Mason, OH (US); Gregory J. Bakos, Mason, OH (US)

(73) Assignee: Ethicon LLC, Guaynabo, PR (US)

( * ) Notice: Subject to any disclaimer, the term of this patent is extended or adjusted under 35 U.S.C. 154(b) by 355 days.

(21) Appl. No.: 15/637,696

(22) Filed: Jun. 29, 2017

(65) Prior Publication Data

US 2019/0000506 A1 Jan. 3, 2019

(51) Int. Cl.
*A61B 17/34* (2006.01)
*A61B 17/00* (2006.01)
(Continued)

(52) U.S. Cl.
CPC ...... *A61B 17/3423* (2013.01); *A61B 17/0057* (2013.01); *A61B 17/0469* (2013.01);
(Continued)

(58) Field of Classification Search
CPC ............ A61B 17/0057; A61B 17/0469; A61B 17/0482; A61B 17/320016;
(Continued)

(56) References Cited

U.S. PATENT DOCUMENTS 5,507,755 A 4/1996 Gresl et al.
5,792,135 A 8/1998 Madhani et al.
(Continued)

FOREIGN PATENT DOCUMENTS

WO WO 2013/101730 A2 7/2013

OTHER PUBLICATIONS

U.S. Appl. No. 15/637,690, filed Jun. 29, 2017.
(Continued)

*Primary Examiner* — Mohamed G Gabr
(74) *Attorney, Agent, or Firm* — Frost Brown Todd LLC

(57) ABSTRACT

An obturator configured for use with a trocar includes a head and a distally extending shaft configured to be received within a working channel of a trocar. The obturator further includes a distal tip configured to puncture tissue, first and second needle entrance ports each arranged on at least one of the head or the shaft, and first and second needle exit ports arranged on the shaft. The first and second needle entrance ports communicate with the first and second needle exit ports, respectively, to define respective first and second suture paths extending obliquely to the central axis. Each of the first and second suture paths includes at least one sealing element. In some examples, the obturator further includes at least one deployable member coupled to the shaft and configured to project radially outwardly in a deployed position.

20 Claims, 20 Drawing Sheets

(51) Int. Cl.
 *A61B 17/04* (2006.01)
 *A61B 17/32* (2006.01)

(52) U.S. Cl.
 CPC ...... *A61B 17/0482* (2013.01); *A61B 17/3474* (2013.01); *A61B 17/320016* (2013.01); *A61B 17/3496* (2013.01); *A61B 2017/00637* (2013.01); *A61B 2017/00663* (2013.01); *A61B 2017/00986* (2013.01); *A61B 2017/3484* (2013.01); *A61B 2017/3488* (2013.01)

(58) Field of Classification Search
 CPC ............ A61B 17/3423; A61B 17/3474; A61B 17/3496; A61B 2017/00986; A61B 2017/3484; A61B 2017/3488
 See application file for complete search history.

(56) References Cited

U.S. PATENT DOCUMENTS

| | | | |
|---|---|---|---|
| 5,817,084 A | 10/1998 | Jensen | |
| 5,878,193 A | 3/1999 | Wang et al. | |
| 6,231,565 B1 | 5/2001 | Tovey et al. | |
| 6,364,888 B1 | 4/2002 | Niemeyer et al. | |
| 6,783,524 B2 | 8/2004 | Anderson et al. | |
| 7,524,320 B2 | 4/2009 | Tierney | |
| 7,691,098 B2 | 4/2010 | Wallace et al. | |
| 7,806,891 B2 | 10/2010 | Nowlin et al. | |
| 7,981,092 B2 | 7/2011 | Duke | |
| 8,226,553 B2 | 7/2012 | Shelton, IV et al. | |
| 8,251,900 B2 | 8/2012 | Ortiz et al. | |
| 8,479,969 B2 | 7/2013 | Shelton, IV | |
| 8,568,362 B2 | 10/2013 | Moreno et al. | |
| 8,573,461 B2 | 11/2013 | Shelton, IV et al. | |
| 8,573,465 B2 | 11/2013 | Shelton, IV | |
| 8,579,807 B2 | 11/2013 | Moreno et al. | |
| 8,602,288 B2 | 12/2013 | Shelton, IV et al. | |
| 8,616,431 B2 | 12/2013 | Timm et al. | |
| 8,636,686 B2 | 1/2014 | Minnelli et al. | |
| 8,690,831 B2 | 4/2014 | Duke | |
| 8,783,541 B2 | 7/2014 | Shelton, IV et al. | |
| 8,800,838 B2 | 8/2014 | Shelton, IV | |
| 8,820,605 B2 | 9/2014 | Shelton, IV | |
| 8,844,789 B2 | 9/2014 | Shelton, IV et al. | |
| 9,301,759 B2 | 4/2016 | Spivey et al. | |
| 9,687,226 B2 | 6/2017 | Hodgkinson et al. | |
| 9,700,303 B2 | 7/2017 | Prior et al. | |
| 2008/0200950 A1 | 8/2008 | Wohlert | |
| 2012/0035623 A1* | 2/2012 | Bagaoisan | A61B 17/0057 606/144 |
| 2013/0035699 A1 | 2/2013 | Heneveld et al. | |
| 2013/0079597 A1* | 3/2013 | Auerbach | A61B 17/0482 600/204 |
| 2013/0310856 A1 | 11/2013 | Sherts et al. | |
| 2014/0350576 A1 | 11/2014 | Patel et al. | |
| 2015/0038793 A1* | 2/2015 | Prior | A61M 5/329 600/204 |
| 2015/0038800 A1* | 2/2015 | Prior | A61B 17/0057 600/235 |
| 2017/0007296 A1* | 1/2017 | Dannaher | A61B 17/34 |
| 2017/0281154 A1 | 10/2017 | Hess et al. | |

OTHER PUBLICATIONS

U.S. Appl. No. 15/637,702, filed Jun. 29, 2017.
U.S. Appl. No. 15/637,683, filed Jun. 29, 2017.
U.S. Appl. No. 15/637,688, filed Jun. 29, 2017.
U.S. Appl. No. 15/637,712, filed Jun. 29, 2017.
U.S. Appl. No. 15/637,707, filed Jun. 29, 2017.
U.S. Appl. No. 15/637,735, filed Jun. 29, 2017.
U.S. Appl. No. 15/637,778, filed Jun. 29, 2017.
Partial European Search Report dated Aug. 16, 2018 for Application No. 18180482.4, 13 pages.
Extended European Search Report dated Nov. 19, 2018 for Application No. 18180482.4, 11 pages.
International Search Report and Written Opinion dated Oct. 5, 2018 for International Application No. PCT/IB2018/054544, 17 pages.

* cited by examiner

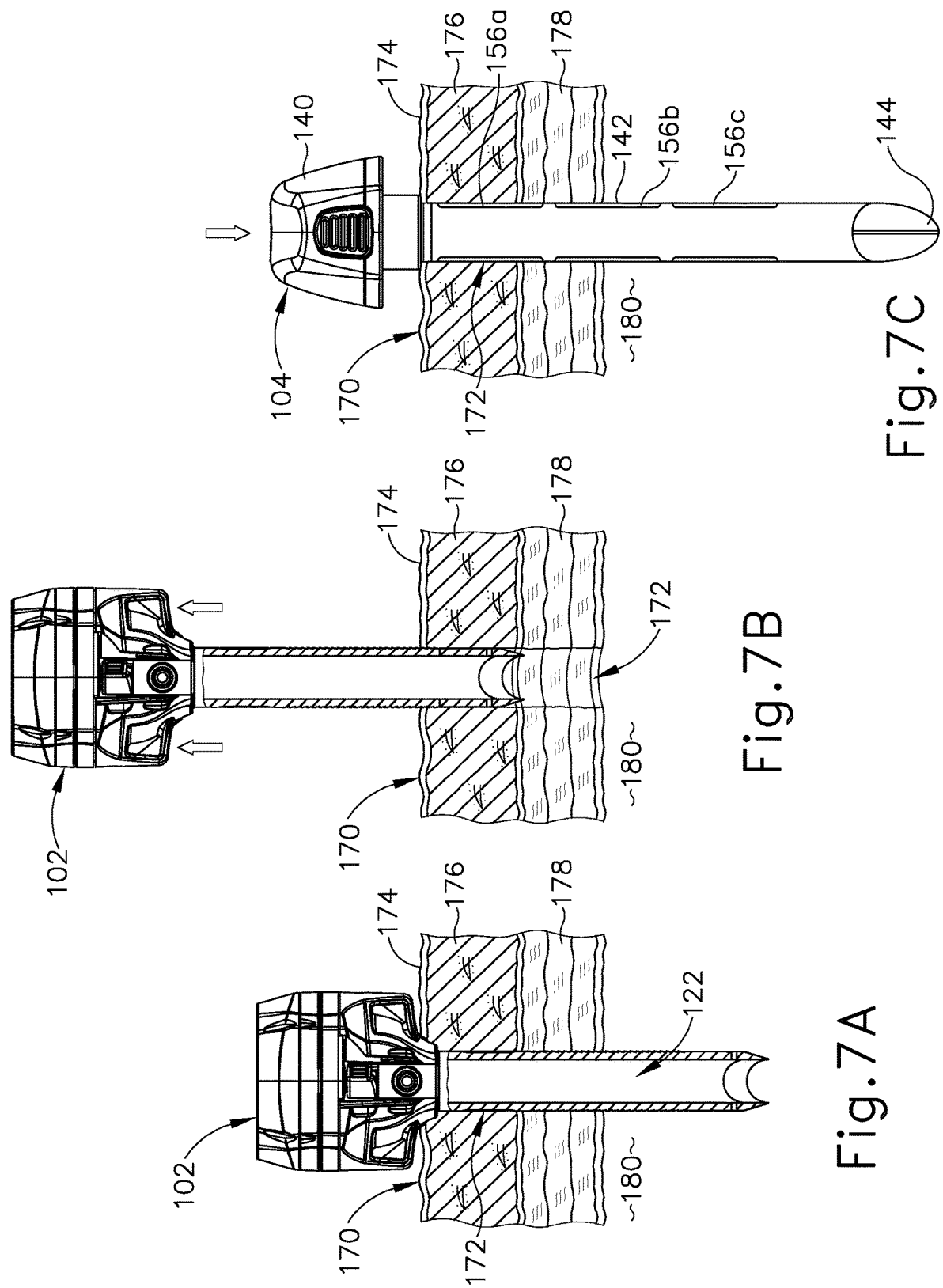

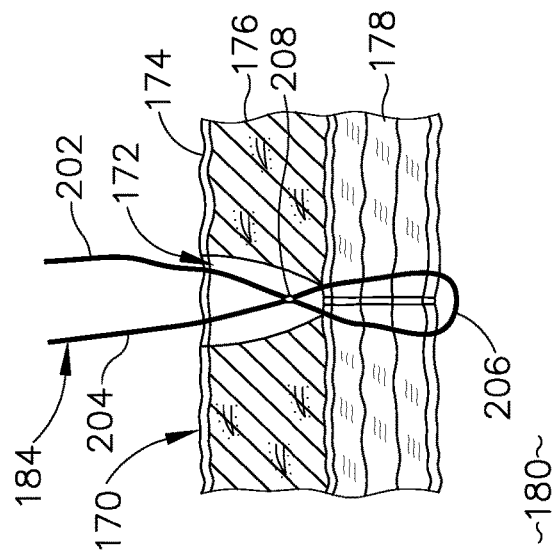
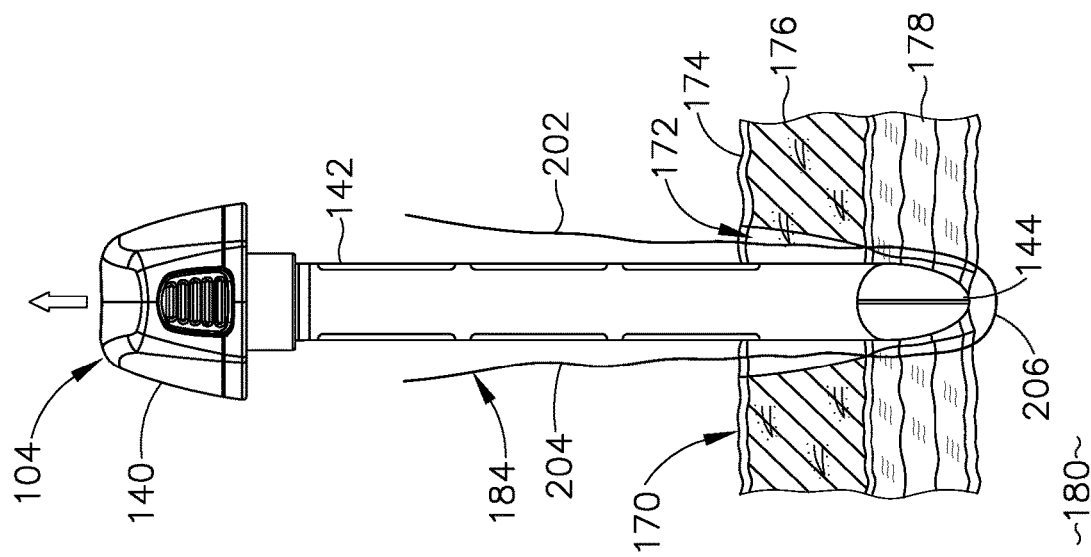
Fig. 7I
Fig. 7H

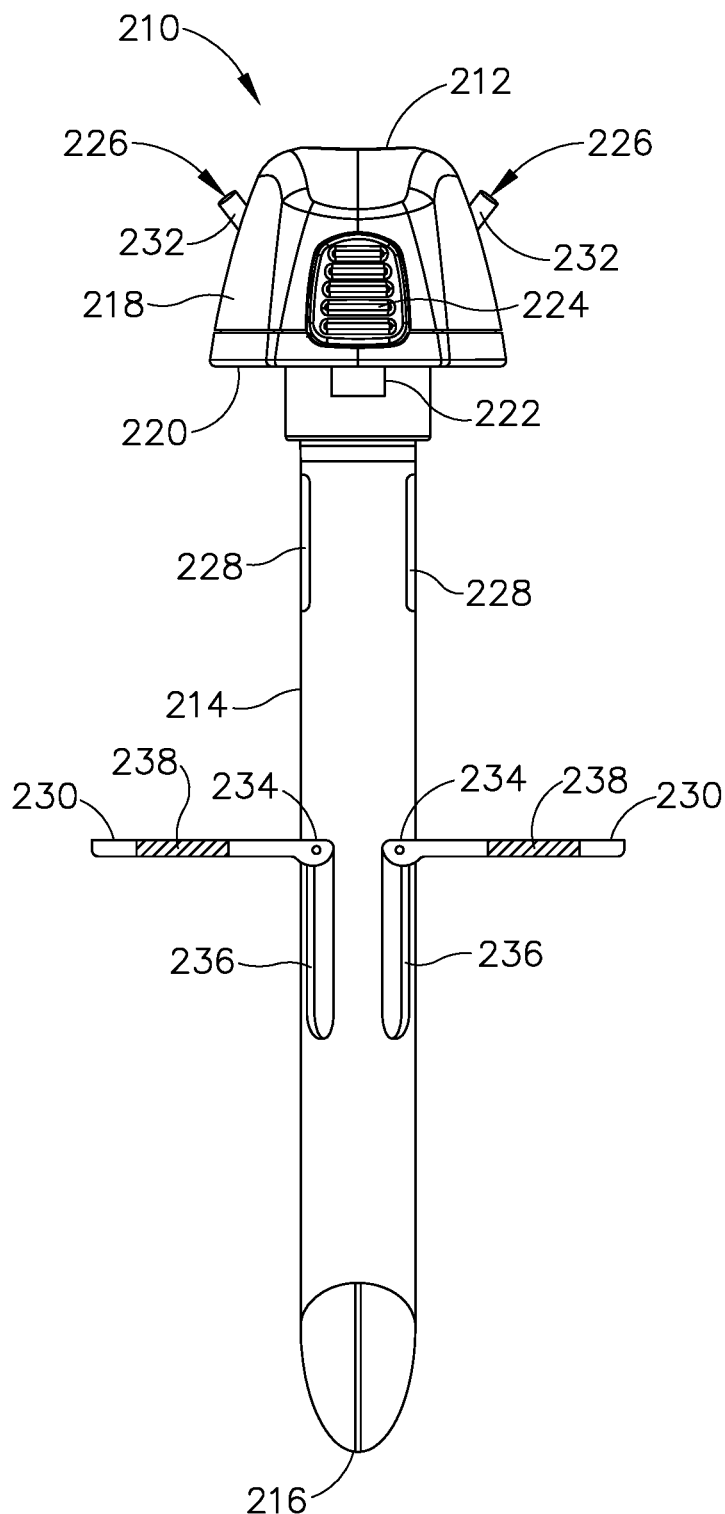
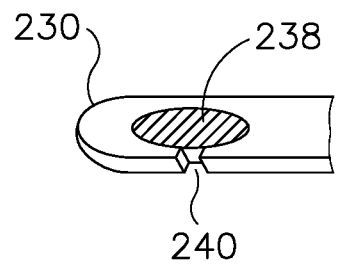
Fig.8A
Fig.8B

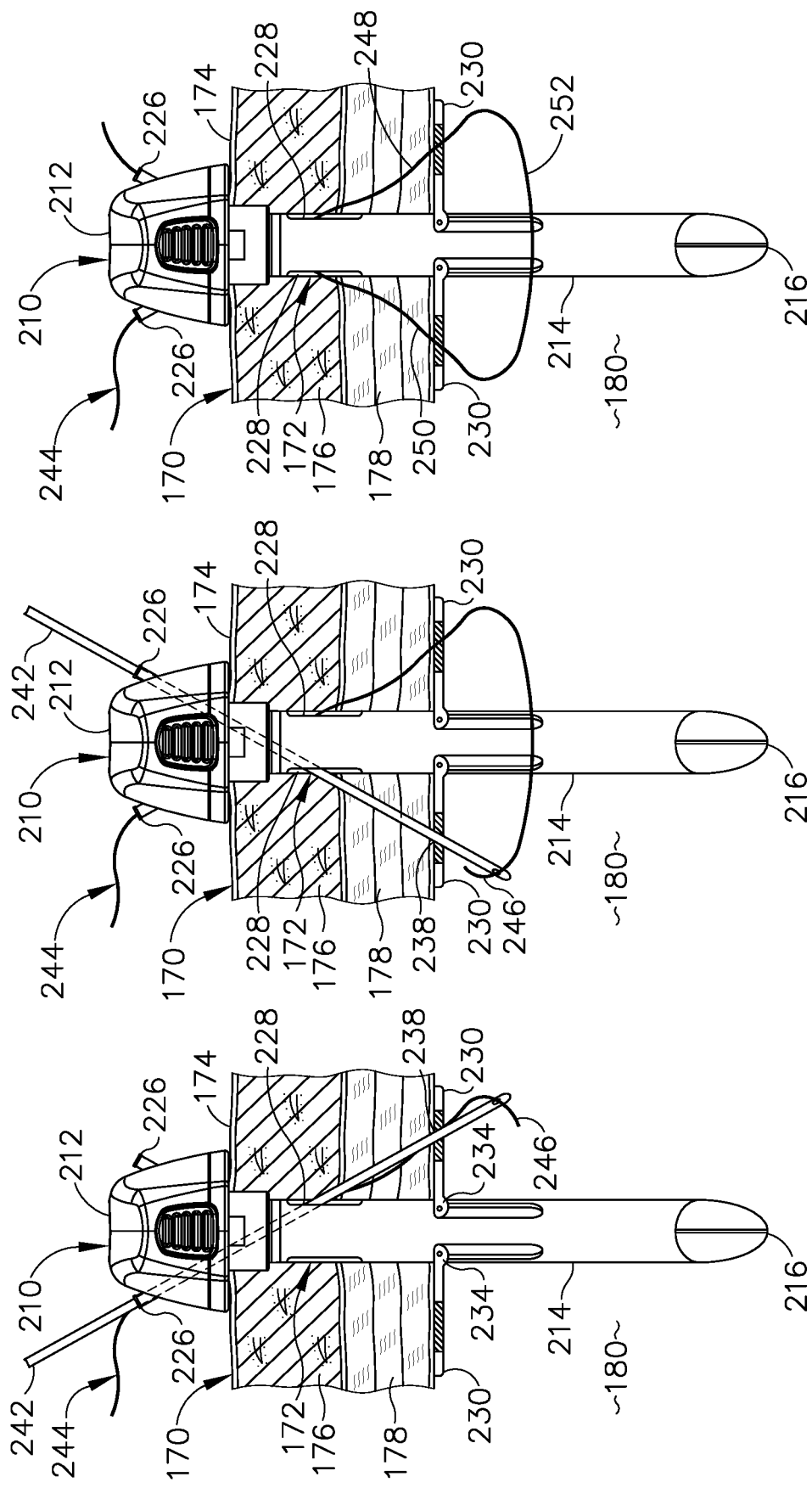

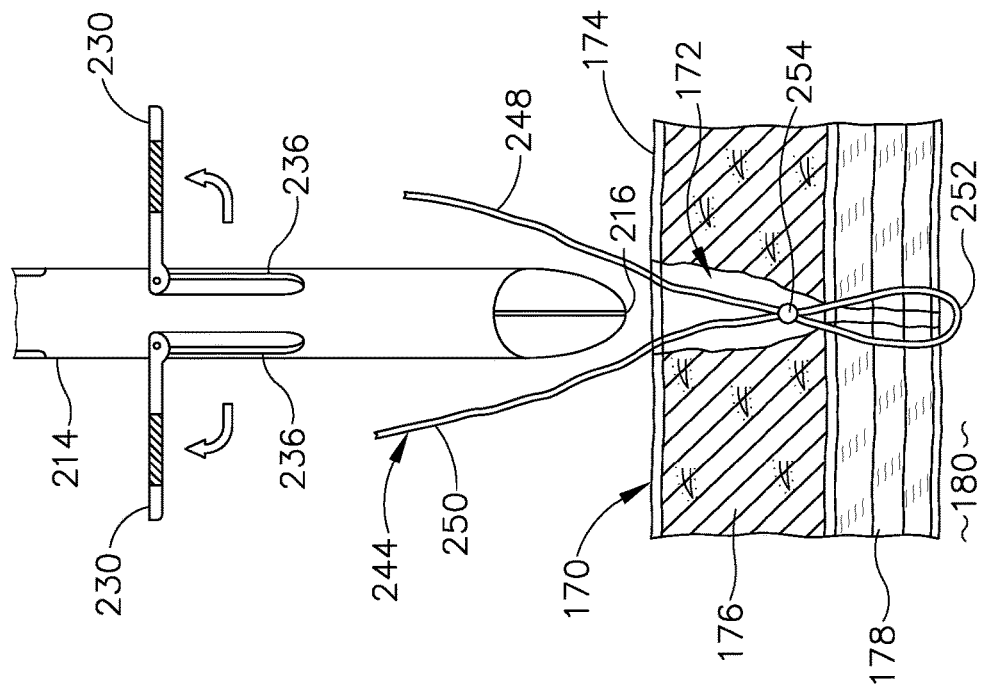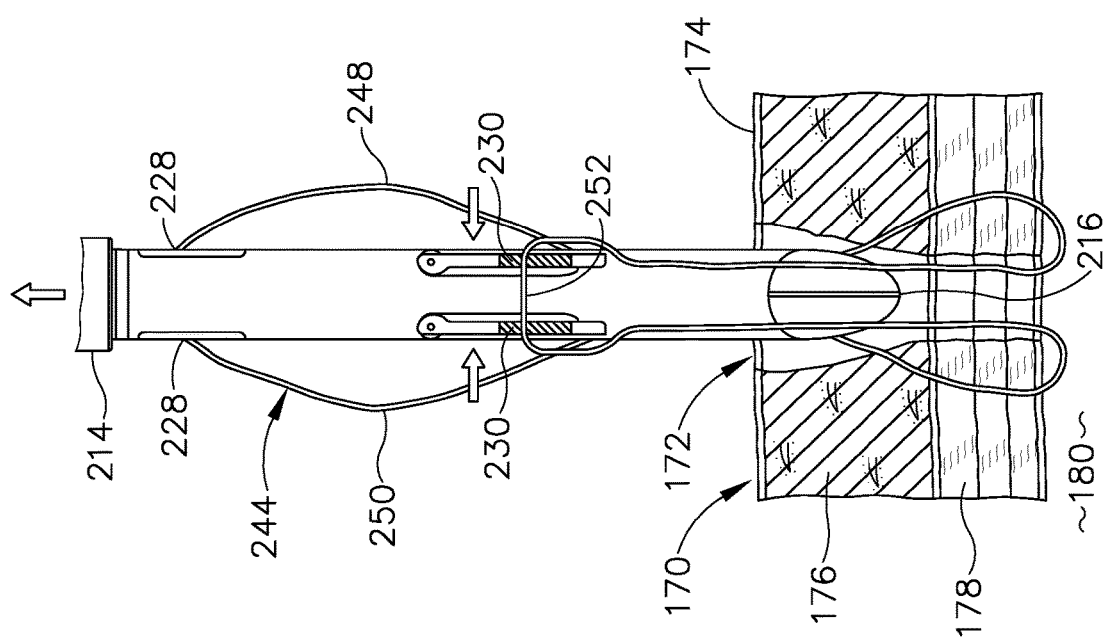

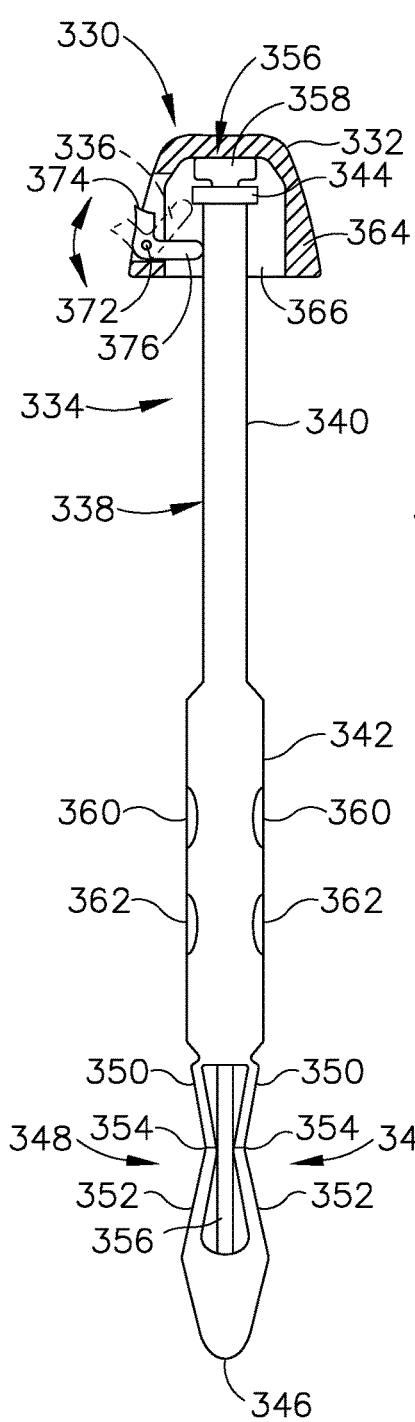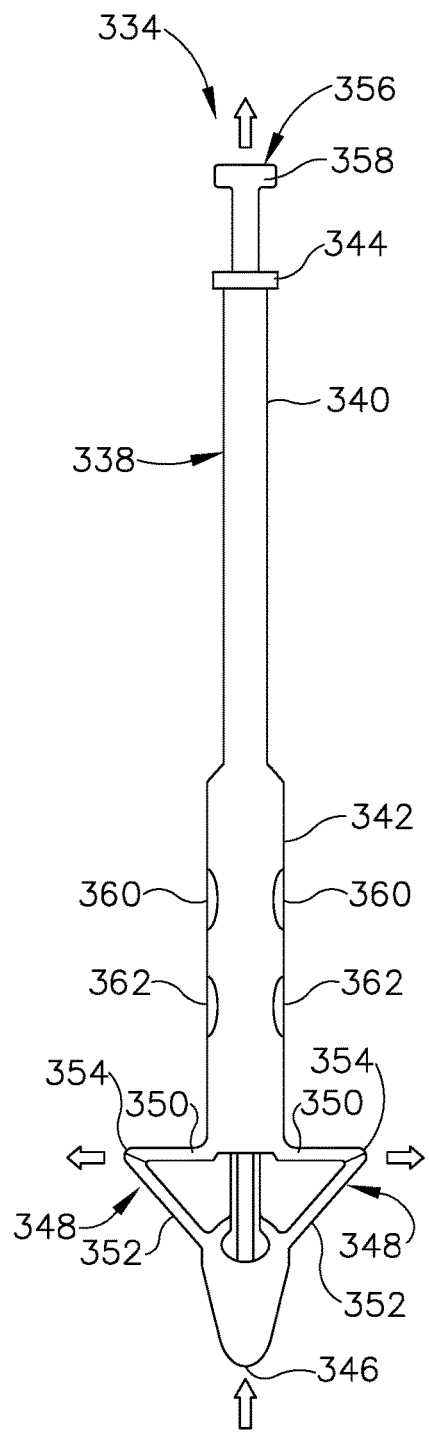
Fig.13　　Fig.14A　　Fig.14B

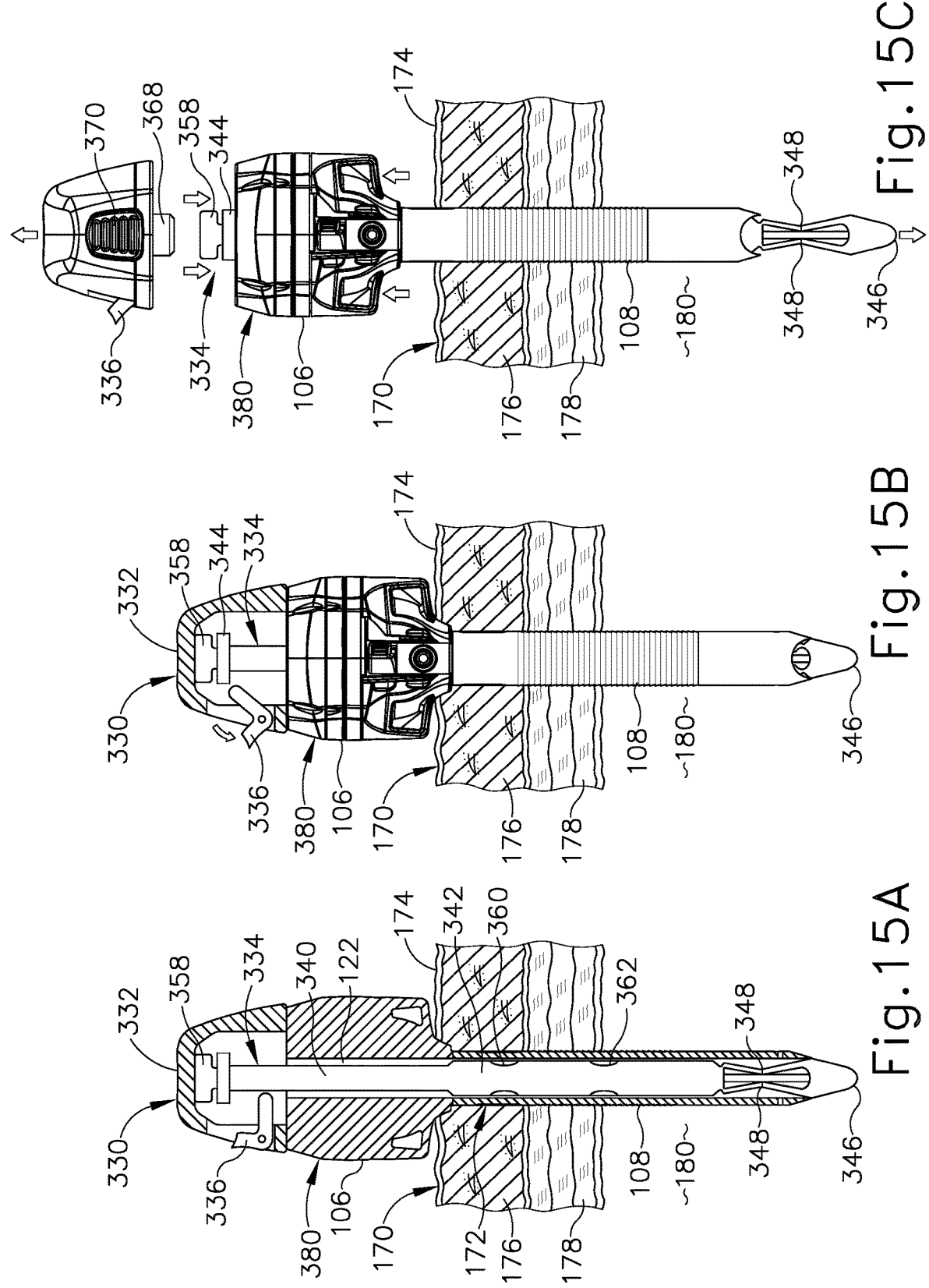

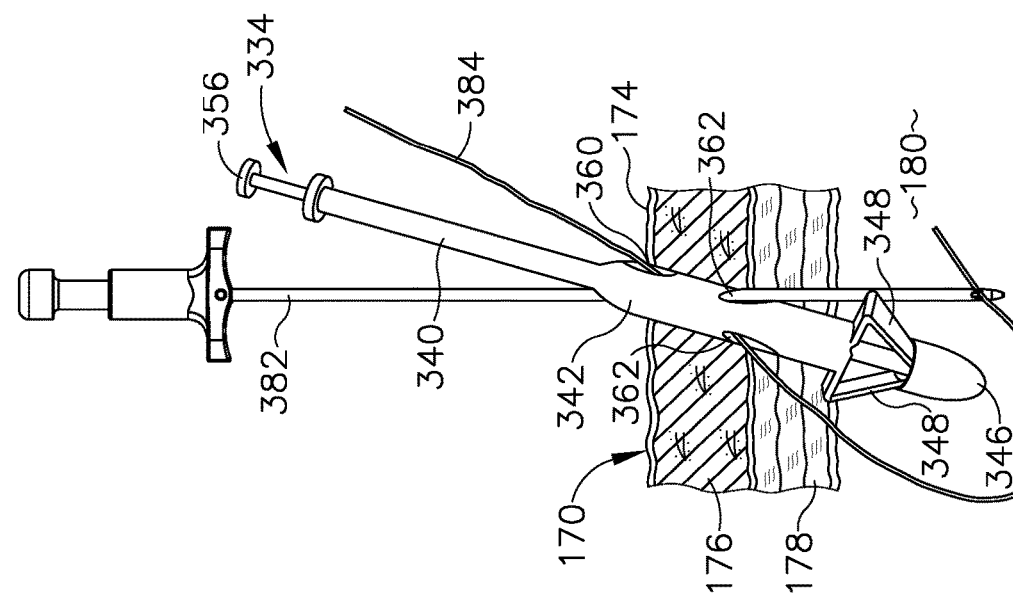
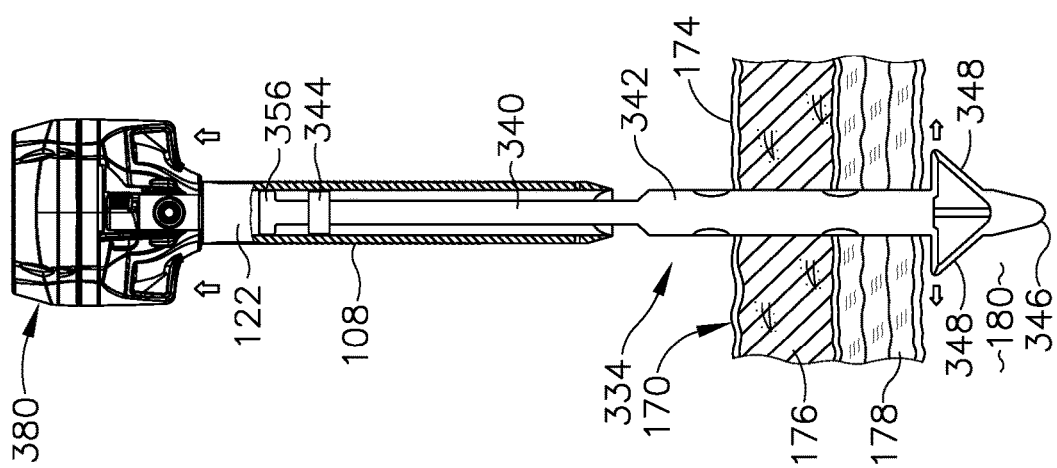
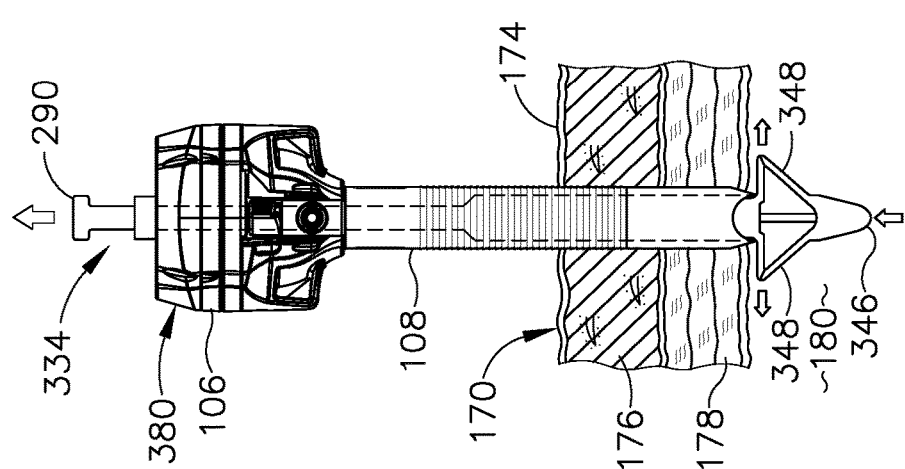

TROCAR OBTURATOR WITH TRANSVERSE NEEDLE PORTS

BACKGROUND

Surgical procedures may require a clinician to gain access to a cavity or other desirable surgical site within a body of a patient. To perform such a surgical procedure, an incision may be made through a tissue of the patient into the cavity. Some conventional surgical procedures may apply a knife, such as a scalpel, to the tissue for the incision, while some less invasive surgical procedures, such as laparoscopic and endoscopic surgical procedures, may access the cavity through a trocar assembly. Traditional trocar assemblies generally include a trocar obturator received within a trocar cannula. In use, the clinician directs the trocar obturator and the cannula through the tissue in order to access the cavity of the desirable surgical site. Once accessed, the clinician withdraws the trocar obturator from the trocar cannula so that the trocar cannula may be used to introduce surgical instruments into the cavity for treatment.

Examples of trocar assemblies, components thereof, and other varieties of surgical access devices and wound closure devices are provided for in U.S. Pat. No. 7,981,092, entitled "Vibratory Trocar," issued Jul. 19, 2011; U.S. Pat. No. 8,226,553, entitled "Access Device with Insert," issued on Jul. 24, 2012; U.S. Pat. No. 8,251,900, entitled "Surgical Access Devices and Methods Providing Seal Movement in Predefined Paths," issued on Aug. 28, 2012; U.S. Pat. No. 8,579,807, entitled "Absorbing Fluids in a Surgical Access Device," issued on Nov. 12, 2013; U.S. Pat. No. 8,568,362, entitled "Surgical Access Device with Sorbents," issued on Oct. 29, 2013; U.S. Pat. No. 8,636,686, entitled "Surgical Access Device," issued on Jan. 28, 2014; U.S. Pat. No. 8,690,831, entitled "Gas Jet Fluid Removal in a Trocar," issued on Apr. 8, 2014; U.S. Pat. Pub. No. 2008/0200950, entitled "Surgical Hook," published on Aug. 21, 2008; U.S. Pat. Pub. No. 2015/0038793, entitled "Devices, Systems, and Methods for Providing Surgical Access and Facilitating Closure of Surgical Access Openings," published on Feb. 5, 2015; U.S. Pat Pub. No. 2015/0038994, entitled "Devices, Systems, and Methods for Providing Surgical Access and Facilitating Closure of Surgical Access Openings," published on Feb. 5, 2015; and U.S. Pat. Pub. No. 2015/0094741, entitled "Wound Closure Device including Mesh Barrier." Published on Apr. 2, 2015. The disclosure of each of the above-cited U.S. Patents and Publications is incorporated by reference herein.

Surgical instruments for use with such surgical access devices may have a distal end effector for engaging tissue through the access device in a number of ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Laparoscopic and endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the cavity of the patient. Positioning of an end effector may be further facilitated through inclusion of one or more articulation joints or features, enabling the end effector to be selectively articulated or otherwise deflected relative to the longitudinal axis of the shaft.

While various kinds of surgical instruments, including surgical access devices and end effectors, and other associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 7A depicts a schematic side sectional view showing the trocar of FIG. 5 inserted through an opening in tissue to access an internal body cavity of a patient;

FIG. 7B depicts a schematic side sectional view showing proximal removal of the trocar of FIG. 7A from the tissue opening;

FIG. 7C depicts a schematic side sectional view showing insertion of the obturator of FIG. 6 distally through the tissue opening;

FIG. 7H depicts a schematic side sectional view of the obturator and tissue of FIG. 7G, showing proximal withdrawal of the obturator from the tissue opening and release of the suture thread from the obturator;

FIG. 7I depicts a schematic side sectional view of the tissue and suture thread of FIG. 7H, showing formation of a suture knot that closes a distal portion of the tissue opening;

FIG. 8A depicts a side elevational view of another exemplary trocar obturator configured for use as a wound closure device, showing needle guide arms of the obturator arranged in deployed positions;

FIG. 8B depicts an enlarged top perspective view of a needle guide arm of the obturator of FIG. 8A;

FIG. 9A depicts a schematic side sectional view of the obturator of FIG. 8A positioned within an opening in tissue to a patient body cavity, showing insertion of a suture passer needle and a suture thread end distally through the obturator, tissue fascia, and first needle guide arm along a first suture path defining a first oblique angle relative to a central axis of the obturator;

FIG. 9B depicts a schematic side sectional view of the obturator and tissue of FIG. 9A, showing insertion of a suture passer needle distally through the obturator, tissue fascia, and second needle guide arm along a second suture path defining a second oblique angle relative to a central axis of the obturator, showing the suture thread end being captured by a distal end of the suture passer needle within the body cavity;

FIG. 9C depicts a schematic side sectional view of the obturator and tissue of FIG. 9B, following proximal withdrawal of the suture passer needle along the second suture path, showing first and second portions of the suture thread extending through the obturator and tissue fascia along the respective first and second suture paths;

FIG. 9D depicts a schematic side sectional view of the obturator and tissue of FIG. 9C, showing proximal withdrawal of the obturator from the tissue opening with the needle guide arms in retracted positions;

FIG. 9E depicts a schematic side sectional view of the obturator and tissue of FIG. 9D, showing the needle guide arms in the deployed positions to release the suture thread, and subsequent formation of a suture knot that closes a distal portion of the tissue opening;

FIG. 13 depicts a side partial-sectional view of another exemplary trocar obturator configured for use as a wound closure device, having a shaft assembly and a head releasably coupled to the shaft assembly;

FIG. 14A depicts a side elevational view of the obturator shaft assembly of FIG. 13, showing a plunger in a distal position and anchor feet members in corresponding retracted positions;

FIG. 14B depicts a side elevational view of the obturator shaft assembly of FIG. 14A, showing the plunger in a proximal position and anchor feet members in corresponding deployed positions;

FIG. 15A depicts a schematic side sectional view of a trocar assembly including the obturator of FIG. 13 coupled with a trocar, showing the trocar assembly positioned within a tissue opening;

FIG. 15B depicts a schematic side sectional view of the trocar assembly and tissue of FIG. 15A, showing movement of a latch of the obturator head to an unlatched position FIG. 15C depicts a schematic side sectional view of the trocar assembly and tissue of FIG. 15B, showing removal of the obturator head from the obturator shaft assembly, and simultaneous proximal movement of the trocar and distal movement of the shaft assembly within the trocar to expose the obturator anchor feet members;

FIG. 15D depicts a schematic side sectional view of the trocar assembly and tissue of FIG. 15C, showing proximal actuation of the obturator plunger to deploy the anchor feet within the patient body cavity;

FIG. 15E depicts a schematic side sectional view of the trocar assembly and tissue of FIG. 15D, showing proximal withdrawal of the trocar from the tissue opening while the obturator shaft assembly remains anchored within the tissue opening and passes through a working channel of the trocar; and FIG. 15F depicts a schematic side sectional view of the obturator shaft assembly and tissue of FIG. 15E, showing insertion of a suture passer needle distally through the shaft assembly and tissue fascia along a second oblique suture path to capture a distal thread end of suture thread extending through the shaft assembly and tissue fascia along a first oblique suture path.

Figure 1:
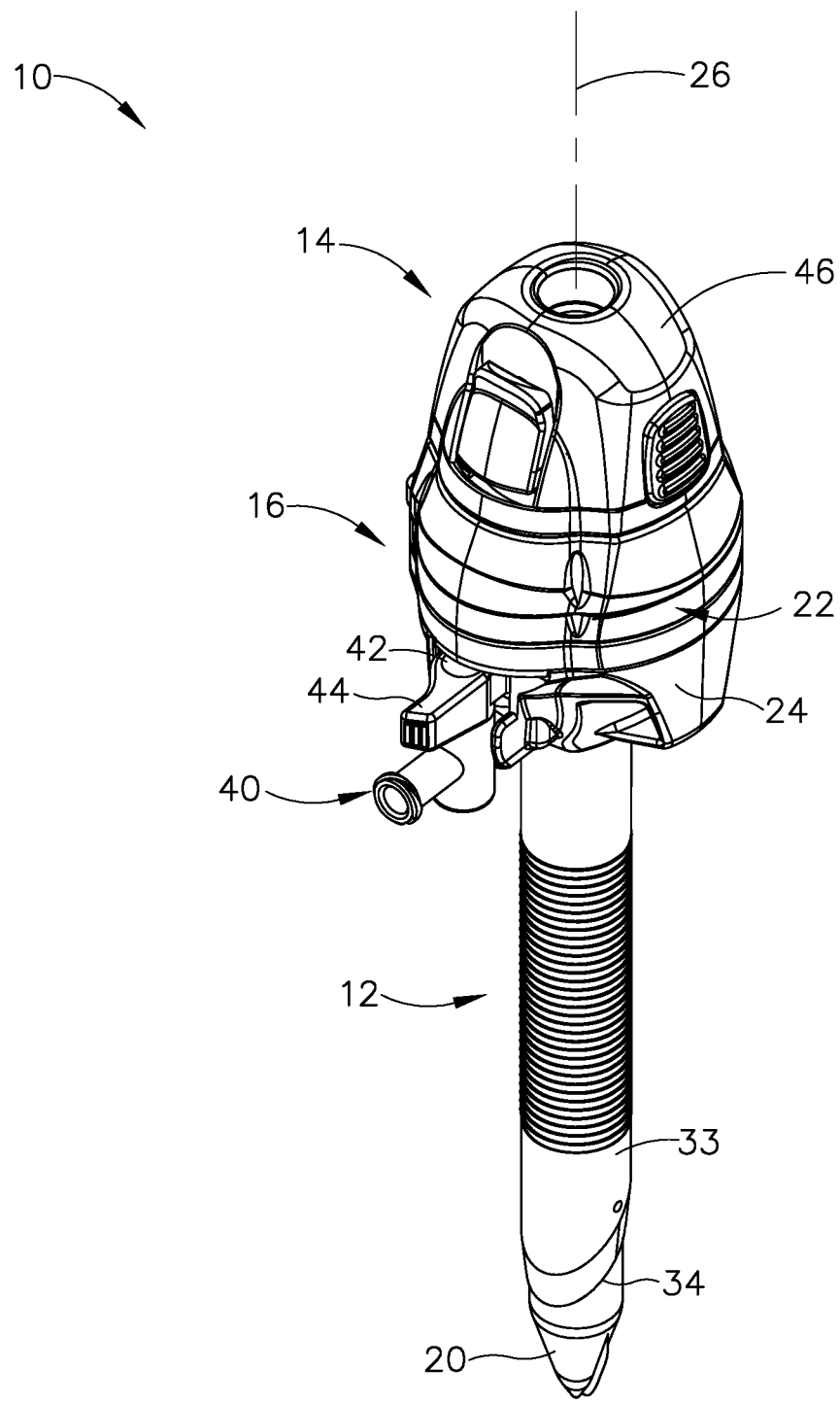
FIG. 1 depicts a perspective view of an exemplary trocar assembly.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. EXEMPLARY SURGICAL ACCESS DEVICE

Figure 2:
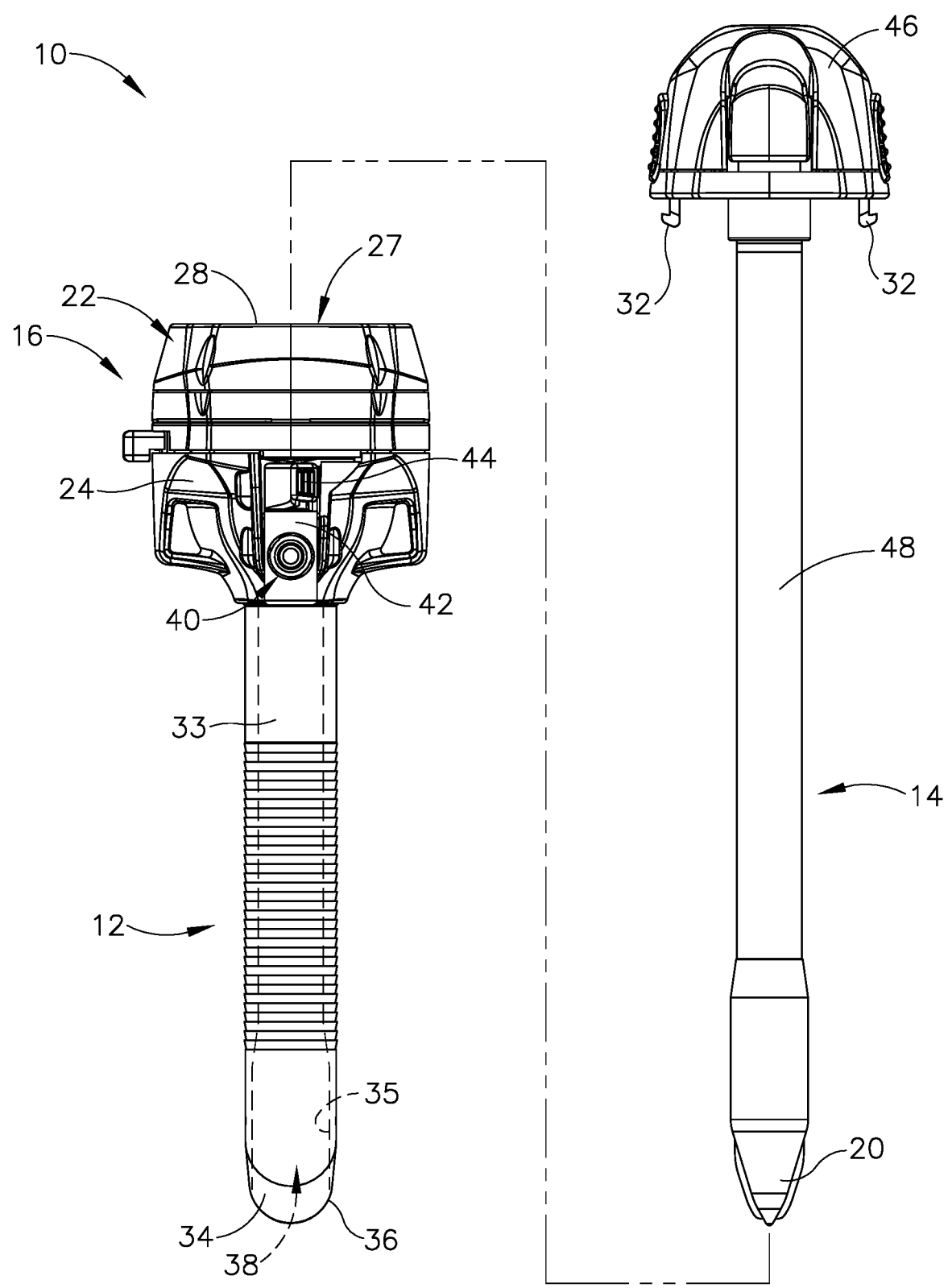
FIG. 2 depicts a partially exploded side elevational view of the trocar assembly of FIG. 1 having a trocar housing, a trocar cannula, and an obturator.

FIGS. 1-2 depict an exemplary surgical access device in the form of a first exemplary trocar assembly (10) that includes a trocar cannula (12) and a trocar obturator (14). Trocar obturator (14) is removably received within trocar cannula (12) through a trocar housing (16) of trocar cannula (12). As shown in FIG. 1 with trocar obturator (14) positioned within trocar cannula (12), a clinician inserts trocar assembly (12) through tissue (17) (see FIG. 3A) of a patient at a desirable surgical site for accessing a cavity (18) (see FIG. 3A) within the patient. By way of example only, trocar assembly (10) may be inserted in a patient's abdomen, between two of the patient's ribs, or elsewhere. A tip (20) of trocar obturator (14) projects distally from trocar cannula (12) to puncture tissue (17) (see FIG. 3A) for introducing a distal end portion of trocar cannula (12) into cavity (18) (see FIG. 3B). The clinician proximally withdraws trocar obturator (14) from trocar cannula (12) such that cavity (18) (see FIG. 3C) within the patient is in communication with a surgical environment via trocar cannula (12). The clinician may then introduce a fluid, such as a gas, through trocar cannula (12) for inflating cavity (18) (see FIG. 3A) and/or an end effector of a surgical instrument through trocar cannula (12) for engaging tissue (17) to achieve a diagnostic or therapeutic effect.

It should be understood that terms such as "proximal" and "distal" are used herein with reference to the clinician gripping trocar housing (16). Thus, tip (20) is distal with respect to the more proximal trocar housing (16). It will be further appreciated that for convenience and clarity, spatial terms such as "vertical" and "horizontal" are used herein with respect to the drawings. However, surgical instruments are used in many orientations and positions, and these terms are not intended to be limiting and absolute. Further, in some instances, components are referred to interchangeably with and without the term "assembly," e.g., a trocar and a trocar assembly. There is no particular intention for the terms to refer to different components. Likewise, terms such as "instrument" and "device" may be used interchangeably.

A. Exemplary Trocar Assembly with Cannula and Obturator

Trocar assembly (10) of FIGS. 1-2 includes cannula (12) extending distally from trocar housing (16). In the present example, trocar housing (16) has a generally cylindrical shape with a proximal removable cap (22) atop a distal housing chamber (not shown). Cap (22) is selectively attachable and detachable from housing chamber (not shown). Trocar housing (16) includes a housing sidewall (24) that extends circumferentially around a central longitudinal axis (26) through trocar assembly (10), and thus along trocar cannula (12). Trocar housing (16) further includes a central lumen (27) extending from a proximal housing end opening (28) to a distal housing end opening (not shown). As shown, cap (22) selectively mates with housing sidewall (24) via distal mating members (not shown) and further includes proximal mating members, such as slots (not shown), configured to removably connect to a pair of tabs (32), respectively, that extend distally from a portion of obturator (14). However, it will be appreciated that alternative structures and devices may also be removably connected to cap (22) during use.

Cannula (12) extends distally from trocar housing (16), and is also generally defined by a cannula sidewall (33) extending circumferentially around central longitudinal axis (26). Cannula sidewall (33) extends distally to a beveled end (34) such that cannula sidewall (33) and beveled end (34) are configured to be inserted through tissue (17) (see FIG. 3A) as discussed below in greater detail for accessing cavity (18) (see FIG. 3A). To this end, cannula (12) generally has a smaller diameter than trocar housing (16), which is configured to remain exterior of tissue (17) (see FIG. 3C). In addition, cannula (12) defines an interior lumen (35) with a proximal cannula end opening (not shown) and a distal cannula end opening (36), which extends through beveled end (34). In the present example, distal housing end opening (not shown) of trocar housing (16) fluidly connects to proximal cannula end opening (not shown) such that central lumen (27) of trocar housing (16) and interior lumen (35) of cannula (12) define a working channel (38). Working channel (38) thus extends from proximal housing end opening (28) to distal cannula end opening (36) and is configured to receive one or more surgical instruments therethrough for accessing cavity (18).

Furthermore, an insufflation port (40) is operatively connected to trocar housing (16) to control the flow of an insufflation fluid, such as carbon dioxide, through a portion of cannula (12) and into cavity (18). More particularly, insufflation port (40) includes a stopcock valve (42) and a cock valve lever (44), which can work together to allow and/or prevent passage of the insufflation fluid into tubing (not shown), through trocar housing (16), and into trocar cannula (12). Trocar housing (16) and cannula (12) respectively have proximal and distal seal assemblies (not shown) positioned within central lumen (27) and interior lumen (35) of working channel (38). In the present example, the proximal seal assembly is an instrument seal (not shown), whereas the distal seal assembly (not shown) is a zero-closure seal, such as a duckbill seal (not shown). Instrument seal (not shown) is retained within cap (22) and is configured to fluidly seal against a surgical instrument extending through working channel (38). In contrast, duckbill seal (not shown) is configured to form a seal in working channel (38) when no instrument is disposed therethrough to thereby inhibit the leakage of insufflation fluid during use. Of course, it will be appreciated that alternative seal assemblies may be positioned within working channel (38) for inhibiting such leakage of insufflation fluid.

Duckbill seal is further configured to be manipulated to provide an opening to working channel (38) that is larger than a corresponding opening provided by instrument seal. This larger opening provided by duckbill seal may facilitate extraction of bodily tissue through trocar housing (16) during a surgical procedure. In particular, cap (22) may be removed, and proximal instrument seal along with it, to expose the duckbill seal and thereby enable a surgeon to extract bodily tissue proximally through the duckbill seal opening that would otherwise be too large to extract proximally through the instrument seal opening.

As discussed briefly above, obturator (14) is used in conjunction with cannula (12) for inserting trocar assembly (10) into the patient. Obturator (14) of the present example, includes a handle head (46) with a cylindrical shaft (48) extending distally therefrom to tip (20), which is generally configured to puncture tissue (17) (see FIG. 3A) as described below in greater detail. Handle head (46) is configured to be gripped by the clinician during use and includes selectively movable tabs (32) extending distally to removably connect with trocar housing (16) for selective securement. Shaft (48) is received through working channel (38) such that tip (20) extends distally from beveled end (34). Of course, obturator (14) may be selectively removed from cannula (12) and trocar housing (16) to free working channel (38) for use. While the present example of trocar assembly (10) has obturator (14), it will be appreciated that cannula (12) may be inserted in some examples without obturator (14) or may be alternatively configured to aid insertion without using obturator (14).

B. Exemplary Method of Accessing a Cavity within a Patient

Figure 3A:
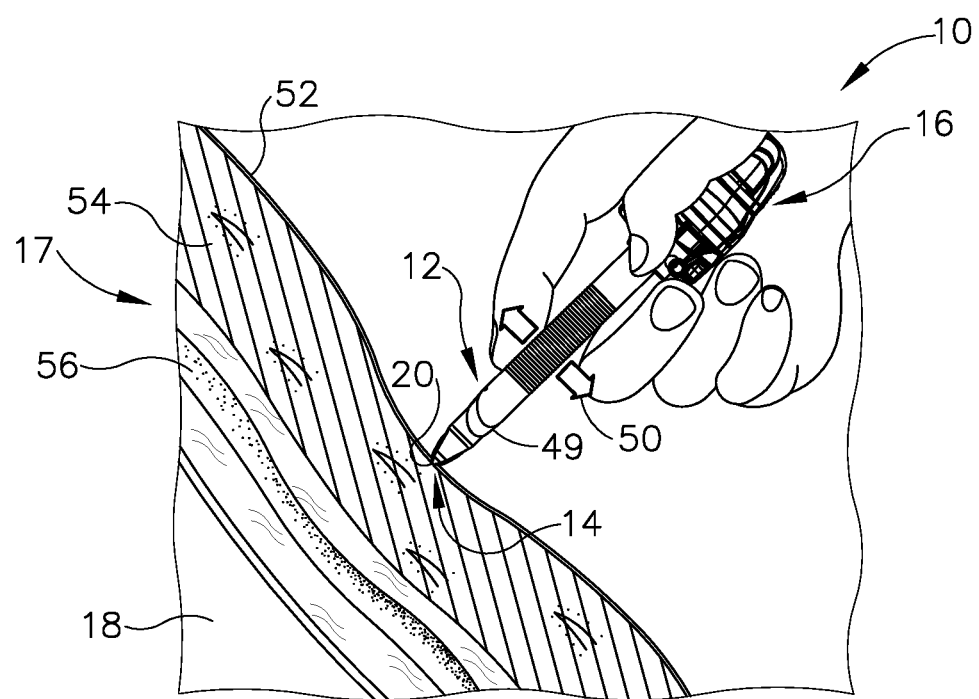
FIG. 3A depicts a side sectional view of tissue of a patient with the trocar assembly of FIG. 1 being manipulated by a clinician through the tissue.
Figure 3B:
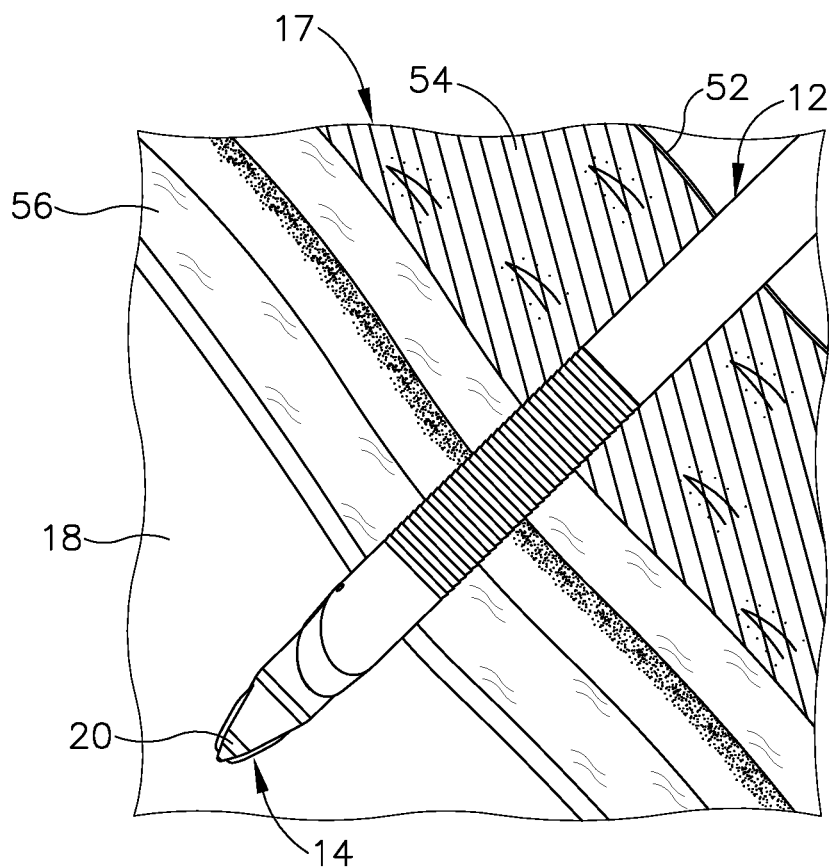
FIG. 3B depicts a side sectional view of the tissue and trocar assembly of FIG. 3A, with the trocar assembly of FIG. 1 inserted through the tissue and received within a cavity of the patient.
Figure 3C:
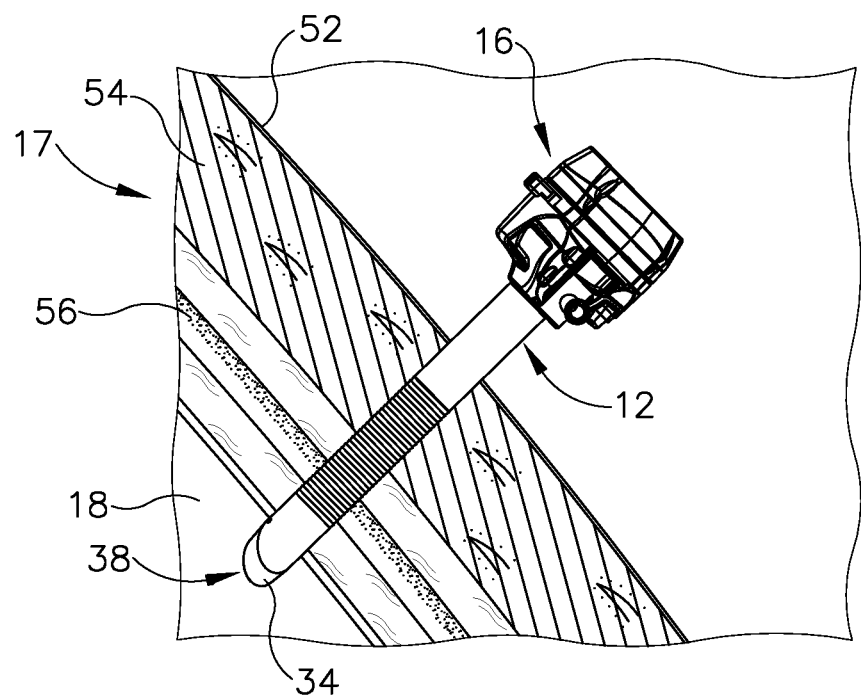
FIG. 3C depicts a side sectional view of the tissue and the trocar assembly of FIG. 3A, with the obturator withdrawn from the trocar cannula for accessing the cavity via a working channel through the trocar cannula and the trocar housing.
Figure 3D:
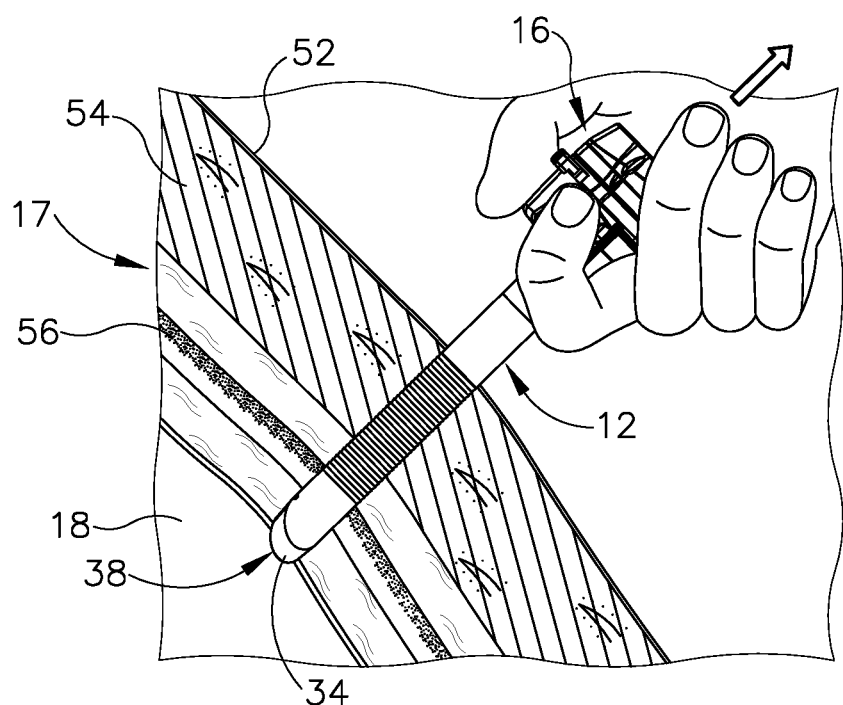
FIG. 3D depicts a side sectional view of the tissue and the trocar assembly of FIG. 3C, with the trocar housing and the trocar cannula being removed from the cavity and the tissue of the patient.

FIGS. 3A-3D illustrate accessing cavity (18) through tissue (17) with trocar assembly (10) discussed above. Tissue (17) of the present example more particularly has relatively outward superficial layers and relatively inward deep layers. Superficial layers generally include an outer layer of skin (52) and an inner layer of fat (54); whereas the deeper layers include layers of fascia (56), which are fibrous and flexible with relatively higher tensile strength than the superficial layers. As shown in FIG. 3A, with obturator (14) received within cannula (12) and connected to trocar housing (16), the clinician manipulates trocar assembly (10) to urge tip (20) of obturator (14) against skin (52) and inward toward cavity (18) while rotating trocar assembly (10) back and forth. Arrow (49) and arrow (50) respectively indicate this inward and rotatable movement. Continued inward urging of trocar assembly (10) further directs tip (20) and beveled end (34) of cannula (12) through the layers of fat (54) and fascia (56) and into cavity (18) as shown in FIG. 3B. The clinician then disconnects obturator (14) from trocar housing (16) and withdraws obturator (14) from cannula (12) to establish access from the exterior of tissue (17) into cavity (18) via working channel (38) as shown in FIG. 3C for achieving a diagnostic or therapeutic effect with another surgical instrument (not shown). Once the diagnostic or therapeutic effect is complete, clinician withdraws cannula (12) and trocar housing (16) outwardly for removal from tissue (17) as shown in FIG. 3D.

Figure 4A:
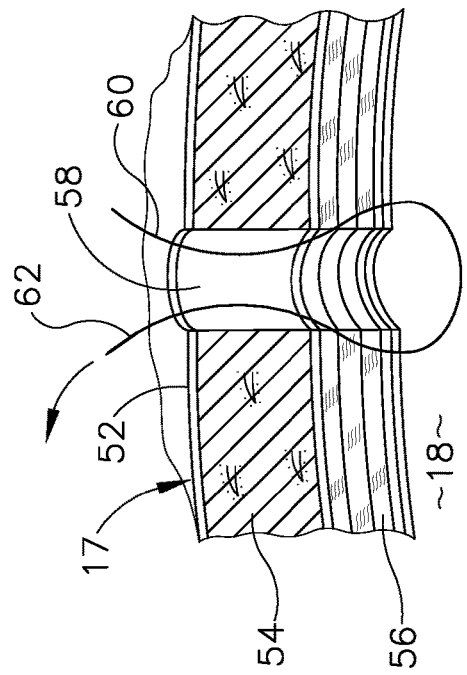
FIG. 4A depicts another side sectional view of the tissue shown in FIGS. 3A-3D following removal of the trocar assembly of FIG. 1, with an opening through the tissue and a suture thread being introduced into a portion of the tissue for suturing the opening closed.
Figure 4B:
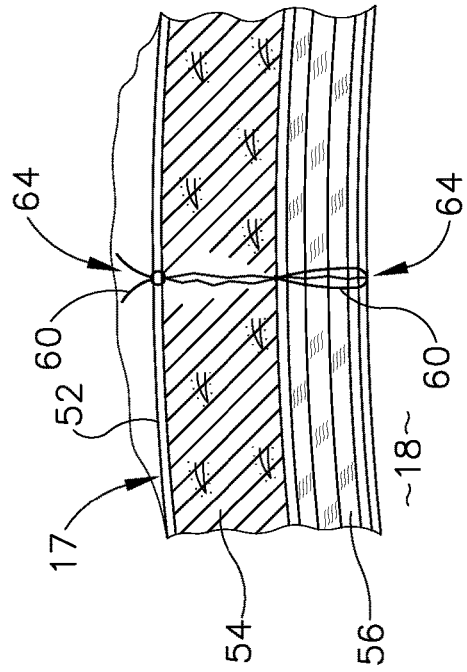
FIG. 4B depicts a side sectional view of the tissue of FIG. 4A, with the suture thread being introduced though another portion of the tissue and pulled through the tissue.
Figure 4C:
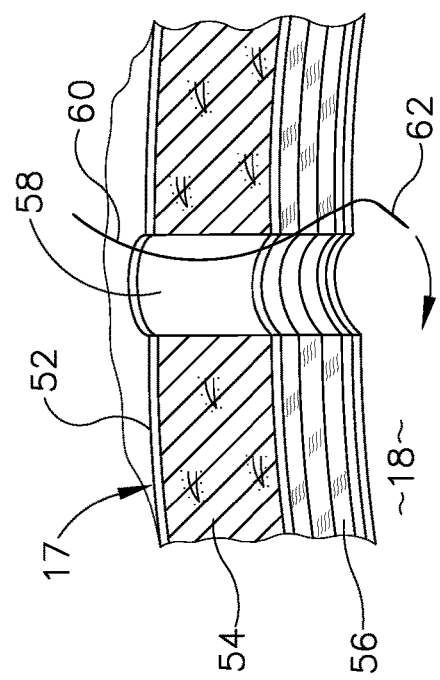
FIG. 4C depicts a side sectional view of the tissue of FIG. 4A, with the suture thread tightened and knotted for at least partially closing the opening.
Figure 4D:
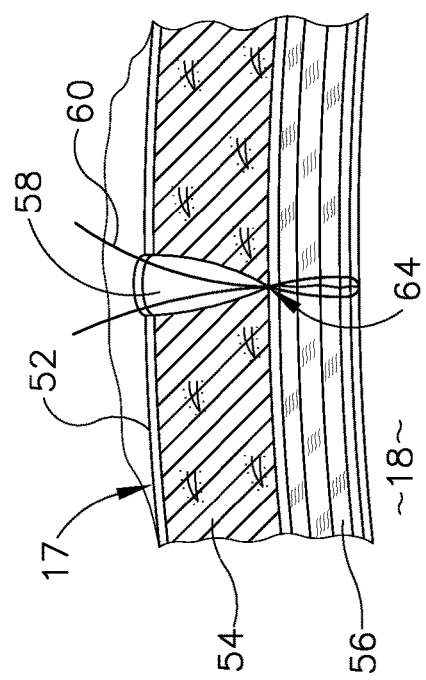
FIG. 4D depicts a side sectional view of the tissue of FIG. 4A, with additional suturing for further closing the opening.

As shown in FIG. 4A, removal of cannula (12) from tissue (17) generally results in a tissue opening (58), which may also be referred to as a tissue port or tissue wound, that clinician closes to encourage healing of tissue (17). While some tissue openings may sufficiently close as tissue (17) comes together, other openings, such as tissue opening (58), are sutured closed with a suture thread (60). In one example shown in FIGS. 4A-4D, suture thread (60) is removably coupled with a needle (62) for guiding suture thread (62) through tissue (17) as the clinician manipulates needle (62). More particularly, as shown in FIG. 4B, the clinician directs needle (62) downwardly through fascia (56) on one side of tissue opening (58) and then upwardly through fascia (56) on the other side of tissue opening (58) as needle (62) clears tissue (17). Notably, the clinician threads needle (62) though fascia (56) a desirable distance distally from tissue opening (58) in order to provide a relatively close proximity to tissue opening (58); but also at a sufficient distance to provide ample fascia (56) for anchoring suture thread (60) therein. Additionally, the clinician angles a tip of needle (62) obliquely away from a central axis of opening (58) at a suitable angle in order to achieve sufficient "bite" when anchoring suture thread (60) within fascia (56). As shown in FIG. 4C, suture thread (60) from respective sides of tissue opening (58) are brought together and pulled to similarly pull tissue (17) together and at least partially close tissue opening (58). The clinician then knots suture thread (60) to secure tissue (17) together and sufficiently close tissue opening (58) with a formed suture (64) as shown in FIG. 4D. Additional sutures (64) may be placed along tissue (17) to further close tissue opening (58) and encourage healing of tissue (17).

While the above described suturing technique shown in FIGS. 4A-4D is one exemplary procedure for closing tissue opening (58) with suture thread (60) following use of trocar assembly (10) (see FIG. 1), other exemplary procedures and devices may be alternatively used for closing such tissue openings. By way of example, U.S. patent application Ser. No. 15/088,723, entitled "Surgical Access Devices with Integrated Wound Closure Features," filed Apr. 1, 2016, which is incorporated by reference herein in its entirety, describes an alternative trocar assembly and suturing technique. To this end, alternative trocar assemblies and suturing techniques may be used in any combination as desired by the clinician.

II. EXEMPLARY SURGICAL ACCESS DEVICE HAVING OBTURATOR CONFIGURED AS WOUND CLOSURE DEVICE

Figure 5:
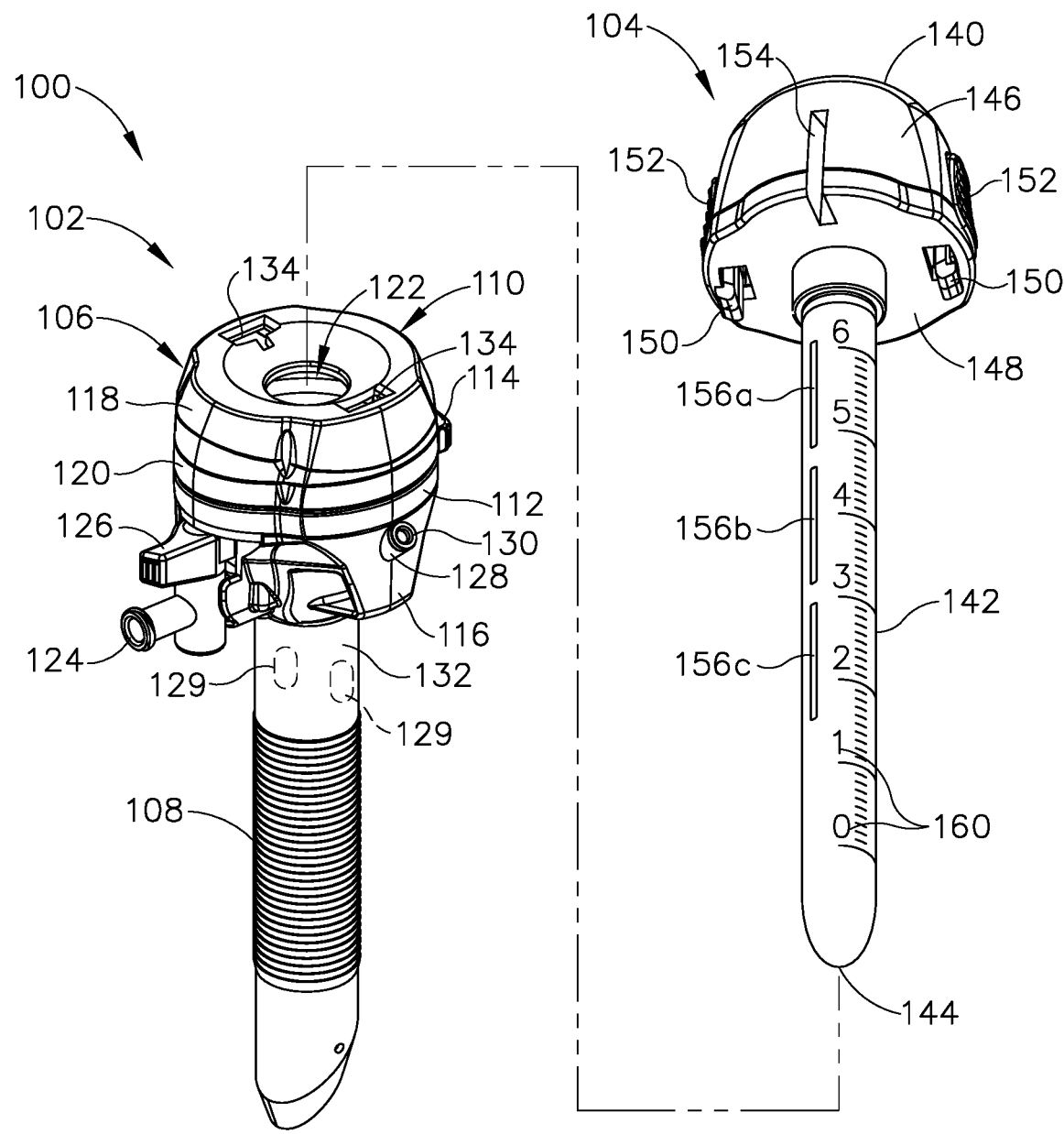
FIG. 5 depicts a disassembled perspective view of an exemplary trocar assembly including a trocar and an obturator configured for use as a wound closure device.

FIG. 5 shows another exemplary surgical access device in the form of trocar assembly (100), which includes a trocar (102) and an obturator (104) configured to releasably couple with trocar (102). Trocar (102) includes a housing assembly (106) and a cannula (108) coupled to and extending distally from housing assembly (106) along a central axis of trocar (102), which coincides with a central axis of trocar assembly (100). Housing assembly (106) includes a proximal housing (110), a housing cap plate (112), a latch ring (114), and a distal housing (116). Proximal housing (110) has a proximal housing head (118) and a proximal housing base (120), and is selectively detachable from the remainder of trocar (102) via actuation (e.g., rotation) of latch ring (114) relative to housing cap plate (112). A central lumen of cannula (108) communicates with an interior of housing assembly (106) to define a working channel (122) extending through trocar (102) along the central axis thereof. Trocar (102) further includes an insufflation port (124) (or "stopcock") having an internal valve (not shown) that is movable between open and closed positions by a valve lever (126). Insufflation tubing (not shown) is coupled to an inlet of insufflation port (124) and directs insufflation fluid, such as carbon monoxide, from a fluid source into insufflation port (124), which directs the fluid distally through working channel (122) into a patient body cavity.

In the present example, trocar (102) is constructed as a wound closure device configured to facilitate suturing of a tissue opening created by trocar (102) during initial insertion through tissue, described above. In that regard, trocar (102) includes a pair of needle guide structures shown in the form of needle guide tubes (128) projecting outwardly from respective side portions of housing assembly (106). Each needle guide tube (128) is configured to direct a suture passer needle (or simply "suture passer") through trocar (102), across working channel (122), at an oblique angle relative to the central axis of trocar (102) to thereby establish an oblique suture path extending through trocar (102) and adjacent tissue to be sutured. Each needle guide tube (128) defines or otherwise communicates with a needle entrance port that opens to working channel (122) through a first side portion of trocar (102) at a proximal location. Each needle guide tube (128) further communicates with a needle exit port (129) that opens to working channel (122) through an opposed second side portion of trocar (102) at a distal location. Each pair of needle entrance and exit ports and their respective needle guide tube (128) cooperate to define a corresponding suture path extending across working channel (122) and through the trocar central axis at an oblique angle relative to the trocar central axis. As used herein, the term "oblique" and variations thereof means neither parallel nor perpendicular to the referenced axis, such as the central axis of trocar (102).

Each needle entrance port and needle exit port (129) of trocar (102) may be provided with a pierceable seal configured to maintain insufflation while a suture passer needle extends through the port, and/or following proximal withdrawal of the suture passer needle from the port. In the present example, trocar (102) includes a seal cap (130) arranged within the entrance end of each needle guide tube (128) and which serves to seal the corresponding needle entrance port. Trocar (102) further includes a cannula sleeve (132) received over a narrowed proximal portion of cannula (108), and which includes a pair of seal protrusions (not shown) projecting radially inwardly from an inner surface of cannula sleeve (132) and into needle exit ports (129) to thereby seal needle exit ports (129). Each seal is configured to be pierced by a suture passer needle directed through trocar (102) along the oblique suture paths.

Trocar (102) may be further configured and operable in accordance with any one or more of the exemplary teachings disclosed in U.S. App. Ser. No. 15/637,683, entitled "Trocar with Oblique Needle Insertion Port and Perpendicular Seal Latch," filed on Jun. 29,2017, issued as U.S. Pat. No. 10,639,068 on May 5, 2020; and U.S. App. Ser. No. 15/637,688, entitled "Trocar with Oblique Needle Insertion Port and Coplanar Stopcock," filed on Jun. 29, 2017, issued as U.S. Pat. No. 10,485,580 on Nov. 26, 2019. The disclosures of these references are incorporated by reference herein.

A. Exemplary Obturator Wound Closure Device Configured to Define Various Suture Path Angles In some instances, it may be desirable to provide suture guide features on an obturator to enable the obturator to function as a wound closure device independently from or in combination with a trocar. In the present example, as described in greater detail below, obturator (104) of trocar assembly (100) is provided with various suture guide features that enable obturator (104) to function as a wound closure device independently from a trocar (102). Advantageously, obturator (104) may be employed to facilitate closure of a tissue opening created by trocar (102) or by various other trocars not having suture guide features.

Figure 6:
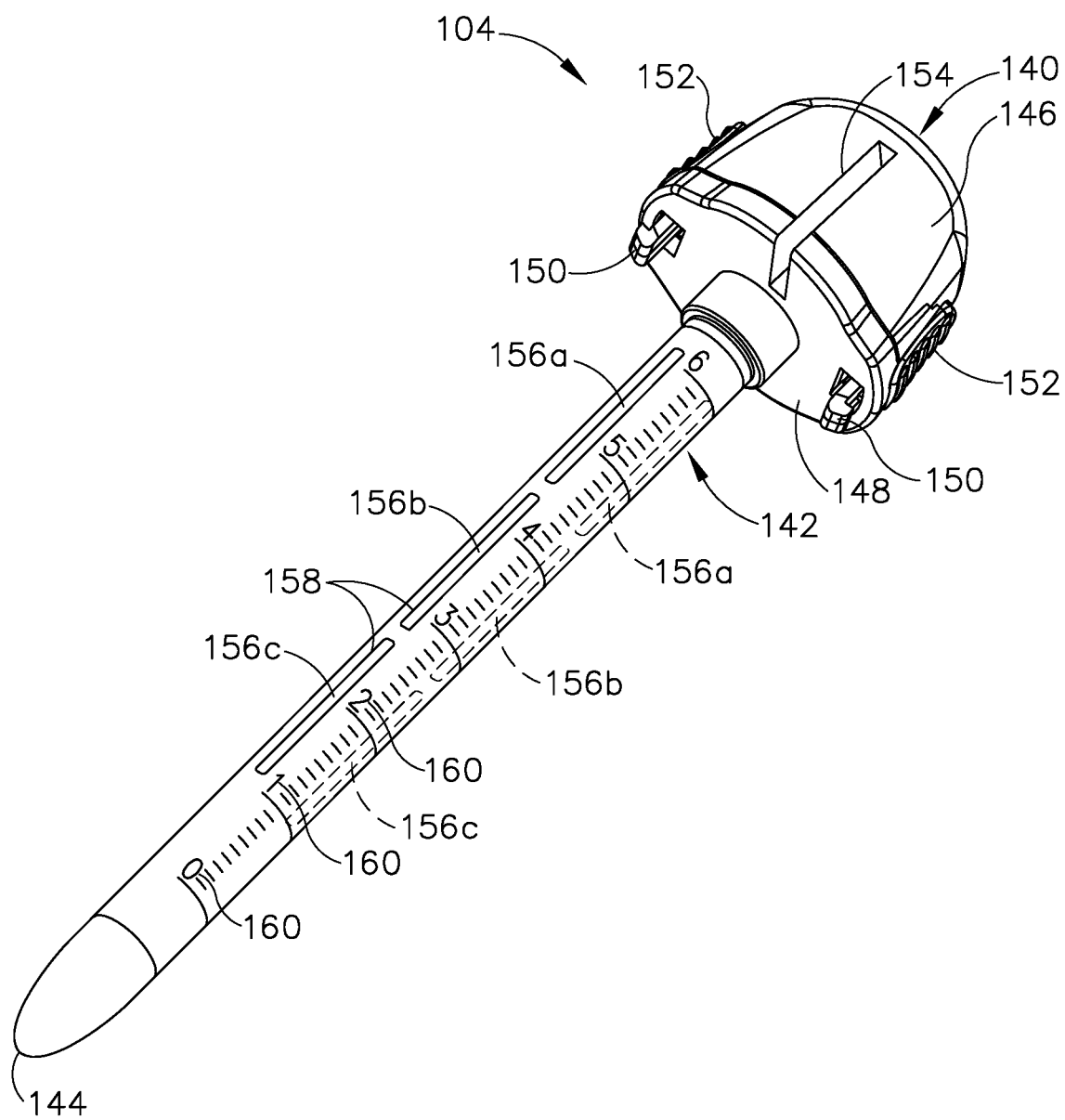
FIG. 6 depicts a perspective view of the obturator of FIG. 5.

As best shown in FIG. 6, obturator (104) of the present example includes a head (140) and a shaft (142) extending distally from head (140) and terminating at a distal tip (144). Shaft (142) is formed with an outer diameter smaller than that of obturator head (140), and is configured to be received within working channel (122) of trocar (102) through a proximal opening formed in proximal housing head (118). Obturator head (140) is configured to function as a handle by which an operator may grasp and manipulate obturator (104). Head (140) includes a circumferentially extending sidewall (146) that tapers proximally, and a distal wall (148) extending generally transverse to a central axis of obturator (104). A pair of tabs (150) depends downwardly from distal wall (148) and is configured to be received within a corresponding pair of slots (134) formed in a proximal face of proximal housing head (118) of trocar (102). Tabs (150) are configured to releasably engage slots (134) to thereby releasably couple obturator (104) with trocar (102). Buttons (152) arranged on sidewall (146) are selectively operable, for example by squeezing, to actuate tabs (150) radially and thereby release tabs (150) from slots (134) so obturator (104) may be separated from trocar (102).

Distal tip (144) of obturator (104) tapers distally to a rounded point configured to puncture tissue. Accordingly, when coupled with trocar (102) via engagement of tabs (150) with slots (134), obturator (104) is configured to facilitate insertion of trocar cannula (108) distally through tissue to thereby establish an opening in the tissue. During insertion, trocar assembly (100) may be grasped and manipulated by obturator head (140). As described above in connection with trocar assembly (10), following insertion of cannula (108) through tissue into a body cavity, obturator (104) is removed from trocar (102) and one or more surgical procedures is performed by inserting a surgical instrument distally through trocar (102) along working channel (122). Following completion of the one or more surgical procedures, trocar (102) is removed from the tissue opening and the tissue opening may be sutured closed using suture guide features provided on obturator (104), as described below. Accordingly, obturator (104) of the present example is operable as both a trocar insertion device and a wound closure device.

As shown best in FIG. 6, obturator (104) includes suture guide features in the form of a pair of needle entrance ports (154) arranged on obturator head (140), and a plurality of needle exit ports (156a, 156b, 156c) arranged on obturator shaft (142). Each needle port (154, 156a, 156b, 156c) opens to an interior of obturator (104), defined by head (140) and shaft (142) in combination, and is configured to guide a suture passer needle distally through the obturator interior along a suture path that defines an angle relative to a central axis of obturator (104) (referred to herein as a "suture path angle") that is oblique, as described in greater detail below.

In the present example, each needle entrance port (154) of obturator (104) is in the form of an elongate slot that extends axially along head sidewall (146) and into a radially outer portion of head distal wall (148). Needle entrance ports (154) are arranged at diametrically opposed positions on obturator head (140), and are spaced circumferentially equidistantly between tabs (150). In other examples, needle entrance ports (154) may be arranged in various other configurations. For instance, needle entrance ports (154) may be arranged in a non-diametrically opposing configuration. Additionally, obturator (104) may include three or more needle entrance ports (154) arranged with uniform or non-uniform circumferential spacing such that no entrance ports (154), or alternatively one or more pairs of needle entrance ports (154), are arranged in a diametrically opposed configuration.

Needle exit ports (156a, 156b, 156c) are in the form of elongate slots that extend axially along obturator shaft (142). In the present example, shaft (142) includes first and second sets of three needle exit ports, arranged on opposing sides of shaft (142): a proximal exit port (156a), a medial exit port (156b), and a distal exit port (156c). Needle exit ports (156a, 156b, 156c) of each set are aligned axially with one another parallel to the obturator central axis, and the first and second sets are arranged at diametrically opposed positions on shaft (142). Each needle entrance port (154) on obturator head (140) cooperates with a respective set of needle exit ports (156a, 156b, 156c) arranged on an opposing side of obturator shaft (142) to guide a suture passer needle along a respective suture path. In the present example, each needle entrance port (154) is diametrically opposed from its respective set of needle exit ports (156a, 156b, 156c). Accordingly, the first and second suture paths defined by needle ports (154, 156a, 156b, 156c) of the present example lie in the same axially extending plane, and intersect to define an X-shaped pattern. In configurations in which the first and second suture paths define the same suture path angle relative to the central axis of obturator (104), the suture paths may intersect generally at the central axis.

Each suture path defined by a needle entrance port (154) and its respective set of needle exit ports (156a, 156b, 156c) may define a variety of oblique suture path angles relative to the obturator central axis, depending on the particular needle exit port (156a, 156b, 156c) through which a suture passer needle exits obturator (104). For instance, a suture passer needle may be directed to exit obturator (104) through: (i) a proximal exit port (156a), to define a first oblique suture path angle suitable for use with tissue of a first thickness; (ii) a medial exit port (156b), to define a second, steeper (i.e., smaller) oblique suture path angle suitable for use with tissue of a second, greater thickness; or (iii) a distal exit port (156c), to define a third, even steeper oblique suture path angle suitable for use with tissue of a third, even greater thickness. Advantageously, the axially elongate shape of each needle exit port (156a, 156b, 156c) enables a suture passer needle to be directed through a selected portion of the needle exit port (156a, 156b, 156c), selected in a proximal-distal direction, to achieve a variety of different suture path angles within the same needle exit port (156a, 156b, 156c).

In the present example, each set of needle exit ports (156a, 156b, 156c) is diametrically opposed from its respective needle entrance port (154) along an axially extending plane containing the central axis of obturator (104). In that regard, as used herein with reference to various first and second structures or reference points, the term "diametrically opposed" and variations thereof is intended to encompass configurations in which the referenced structures are arranged at different longitudinal locations along a referenced axis, such as central axis of obturator (104). For instance, in the present example each needle entrance port (154) is spaced proximally from its respective needle exit ports (156a, 156b, 156c), though the entrance port (154) and its needle exit ports (156a, 156b, 156c) are still understood to be diametrically opposed from one another along the same axially extending plane, as described above. In alternative versions of obturator (104), a needle entrance port (154) may lie in a first plane containing the obturator central axis while the corresponding needle exit ports (156a, 156b, 156c) lie in a second plane containing the obturator central axis. In such versions, the first and second planes may be angularly offset from one another such that the needle entrance port (154) and its respective needle exit ports (156a, 156b, 156c) are not diametrically opposed from one another.

As shown in FIG. 6, each needle exit port (156a, 156b, 156c) is provided with a pierceable seal (158) configured to be pierced by a suture passer needle upon insertion through obturator (104) during a wound closure procedure. Each pierceable seal (158) is configured to support a suture passer needle and suture thread directed therethrough, as well as prevent advancement of tissue and bodily fluids into the obturator interior, and also maintain any remaining insufflation of the patient body cavity. Though not shown, each needle entrance port (154) may be provided with a pierceable seal as well. Further, it will be appreciated that one or more of the needle ports of the additional exemplary obturators (210, 260, 330) described below may be provided with a pierceable seal or other sealing element that provides similar functional benefits. In various examples, such sealing elements may ensure that each of the suture paths extending through the respective obturator (210, 260, 330) remains in a generally sealed state while a suture passer needle is received along the suture path, as well as following proximal withdrawal of the suture passer needle from the obturator (210, 260, 330).

In the present example, obturator shaft (142) further includes visual indicia in the form of tissue depth graduation marks (160) spaced axially along a length of shaft (142). Marks (160) may indicate any suitable distance increments, such as inches or centimeters for example, and subdivisions of each increment. Marks (160) are configured to communicate to a surgeon a depth, measured from a distal end portion of shaft (142), to which shaft (142) has been inserted within patient tissue. For example, during or after insertion of shaft (142) into tissue through a tissue opening, a surgeon may observe a distal-most mark (160) that is visible extracorporeally to determine a depth to which shaft (142) has been inserted into the tissue, which may indicate a thickness of the tissue. The surgeon may account for this depth when determining which needle exit port (156a, 156b, 156c) through which to direct the suture passer needles during a wound closure procedure.

B. Exemplary Wound Closure Procedure Using Obturator Wound Closure Device Configured to Define Various Suture Path Angles FIGS. 7A-7I show steps of an exemplary wound closure procedure (also referred to as a "suturing procedure") for suturing closed a tissue opening (172) formed in tissue (170) of an exemplary thickness, using obturator (104) of trocar assembly (100) as a wound closure device. Like tissue (17) described above, tissue (170) includes outward superficial layers and inward deeper layers. Superficial layers generally include an outer layer of skin (174) and an inner layer of fat (176). The deeper layers include layers of fascia (178), which are fibrous and flexible with relatively higher tensile strength than the superficial layers.

FIG. 7A shows trocar (102) of trocar assembly (100) following completion of one or more surgical procedures in which one or more endoscopic surgical instruments are directed distally through trocar (102), via working channel (122), into body cavity (180) to access tissue therein. FIG. 7B shows proximal removal of trocar from tissue opening (172). FIG. 7C shows insertion of obturator shaft (142) distally through tissue opening (172) so that obturator tip (144) resides within body cavity (180).

Figure 7E:
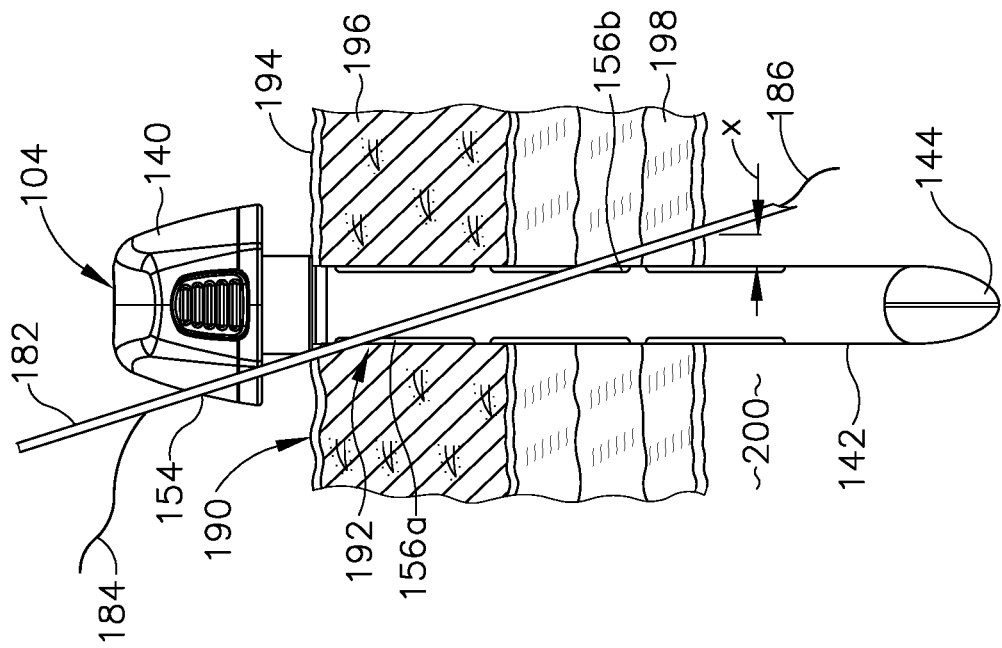
FIG. 7E depicts a schematic side sectional view of the obturator of FIG. 7C positioned within tissue of a second thickness, showing insertion of a suture passer needle and a suture thread end distally through the obturator and tissue fascia along an alternative first suture path defining a second oblique angle relative to the central axis of the obturator.
Figure 7D:
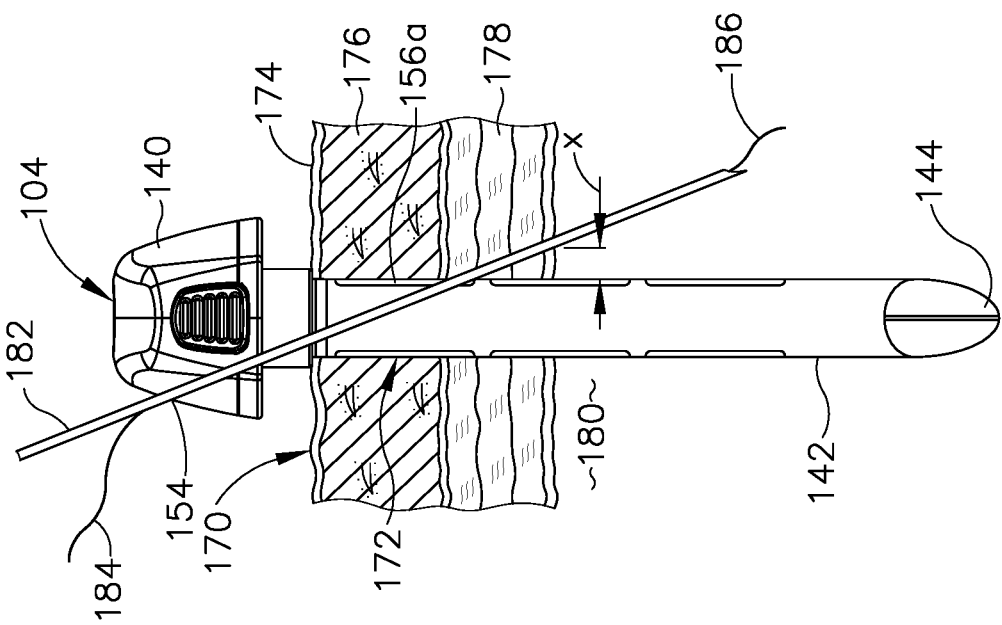
FIG. 7D depicts a schematic side sectional view of the obturator of FIG. 7C positioned within tissue of a first thickness, showing insertion of a suture passer needle and a suture thread end distally through the obturator and tissue fascia along a first suture path defining a first oblique angle relative to a central axis of the obturator.

FIG. 7D shows an exemplary suture passer needle (182) and a suture thread (184) having a thread end (186) directed distally through obturator (104) along an exemplary first suture path. The first suture path extends through a first needle entrance port (154), an interior of obturator (104), an opposed proximal needle exit port (156a), and an adjacent first portion of tissue fascia (178) into body cavity (180). The suture path defines a corresponding first suture path angle relative to the central axis of obturator (104). The suture path and the resulting suture path angle are chosen by a surgeon based on a thickness of tissue (170) and a desired amount of tissue fascia (178) to be captured by suture thread (184) on each side of obturator (104), referred to as "tissue bite." In the present context, tissue bite is defined by a distance (X) measured perpendicularly from the inner wall of tissue opening (172), which may coincide with the outer surface of obturator shaft (142), to the point at which suture passer needle (182) and thus suture thread (184) exits distally from tissue fascia (178) into body cavity (180). In some examples, tissue bite distance (X) may be approximately 1 centimeter.

FIG. 7E shows an exemplary alternative arrangement in which obturator (104) is positioned within a tissue opening (192) formed in tissue (190) of an exemplary second thickness that is greater than the thickness of tissue (170). Like tissue (170), tissue (190) includes an outer layer of skin (194), an upper layer of fat (196), and deeper layers of fascia (198) above body cavity (200). To achieve the same tissue bite distance (X) in tissue (190) as in tissue (170), suture passer needle (182) is directed along a suture path having a steeper suture path angle measured relative to the obturator central axis. In the present example, suture passer needle (182) extends along the suture path through a proximal portion of needle entrance port (154), through an interior of obturator head (140), and exiting from a distal portion of needle entrance port (154). The suture passer needle (182) reenters obturator (104) through a proximal needle port (156a) on a first side of obturator shaft (142), and exits through a medial needle port (156b) on an opposed second side of obturator shaft (142). Accordingly, it will be appreciated that proximal and medial needle exit ports (156a, 156b) on shaft (142) may also function as needle entrance ports when defining suture paths of relatively steeper angles relative to obturator central axis.

Following the steps shown in FIGS. 7D and 7E, suture passer needle (182) is manipulated by a surgeon to release thread end (186) of suture thread (184) within body cavity (180, 200), and suture passer needle is withdrawn proximally from obturator (104). FIG. 7F shows obturator (104) positioned within tissue (170), and suture passer needle (182) being directed distally through obturator (104) along a second suture path extending through a second needle entrance port (154), an opposed proximal needle exit port (156a), and an adjacent second portion of tissue fascia (178), into body cavity (180). Suture passer needle (182) and/or obturator (104), via head (140), are suitably manipulated by a surgeon to capture thread end (186) with a distal tip of suture passer needle (182). Suture passer needle (182) and thread end (186) are then withdrawn proximally along the second suture path.

Figure 7G:
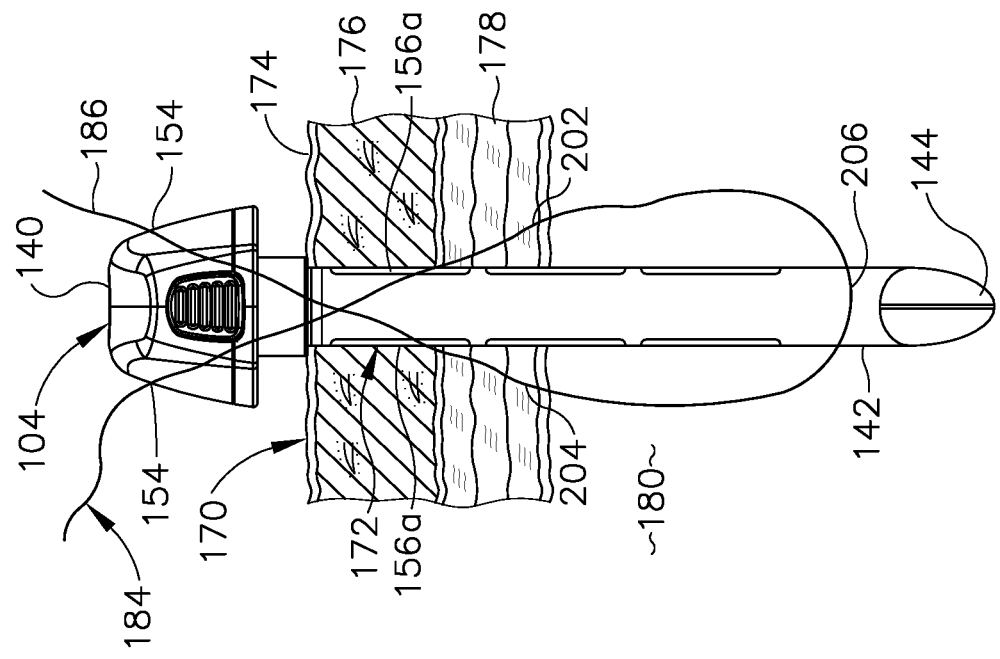
FIG. 7G depicts a schematic side sectional view of the obturator and tissue of FIG. 7F following proximal withdrawal of the suture passer needle along the second suture path, showing first and second portions of the suture thread extending through the obturator and tissue fascia along the respective first and second suture paths.
Figure 7F:
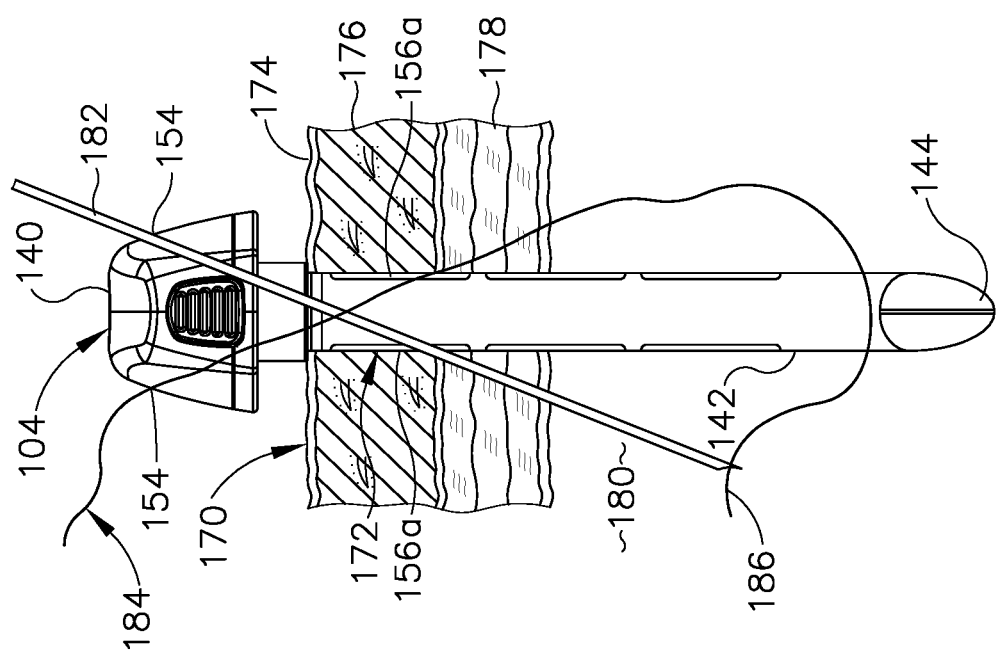
FIG. 7F depicts a schematic side sectional view of the obturator and tissue of FIG. 7D, showing insertion of a suture passer needle distally through the obturator and tissue fascia along a second suture path defining an oblique angle relative to the central axis of the obturator, showing the suture thread end being captured by a distal end of the suture passer needle within the body cavity.

As shown in FIG. 7G, a first thread leg (202) of suture thread (184) extends through obturator (104) and tissue fascia (178) along the first suture path; a second thread leg (204) extends through obturator (104) and tissue fascia (178) along the second suture path; and an anchoring loop (206) extends through body cavity (180) between first and second captured portions of tissue fascia (178). In the present example, the second suture path defines a suture path angle similar to that of the first suture path, shown in FIG. 7D. In alternative examples, however, suture passer needle (182) may be directed through obturator (104) along first and second suture paths having different suture path angles, for example to accommodate nonuniformities in the structure of tissue (170).

As shown in FIG. 7H, once suture thread (184) has been threaded through tissue (170) along the first and second suture paths, obturator (104) is withdrawn proximally from tissue opening (172) to allow thread legs (202, 204) to advance distally through needle ports (154, 156a), thereby releasing suture thread (184) from obturator (104). Thread legs (202, 204) may then be pulled tight to draw together the captured portions of fascia (178) on either side of tissue opening (172), and tied to form a suture knot (208) at a location just proximally of fascia layers (178), as shown in FIG. 7I. Optionally, the remaining portions of thread legs (202, 204) may be directed through fat (176) and skin (174) using suture needles, for example as shown in FIG. 4D, to create an additional "superficial" suture knot to fully close tissue opening (172) and promote optimal healing.

III. EXEMPLARY OBTURATOR WOUND CLOSURE DEVICE HAVING DEPLOYABLE NEEDLE GUIDE ARMS

A. Exemplary Obturator Wound Closure Device

FIGS. 8A and 8B show another exemplary obturator (210) configured for use as a wound closure device. Though not shown, it will be understood that obturator (210) may also be used as a trocar insertion device in combination with any suitable trocar, such as trocar (102) described above. Like obturator (104) described above, obturator (210) is provided with suture guide features that enable obturator (104) to function as a wound closure device independently from a trocar, as described in greater detail below.

Obturator (210) is similar to obturator (104) in that obturator (210) includes a head (212) and a shaft (214) extending distally from head (212) and terminating at a distal tip (216) configured to puncture tissue. Shaft (214) is formed with an outer diameter smaller than that of head (212), and is configured to be received within a working channel of any suitable trocar, such as trocar (102) described above. Head (212) is configured to function as a handle by which an operator may grasp and manipulate obturator (210). Head (212) includes a circumferentially extending sidewall (218) that tapers proximally, and a distal wall (220) extending generally transverse to a central axis of obturator (210). A pair of tabs (222) depends downwardly from distal wall (220) and is configured to be received within a corresponding pair of slots formed in a proximal face of a trocar (not shown), such as slots (134) of trocar (102). Tabs (222) are configured to releasably engage trocar slots to thereby releasably couple obturator (210) with the trocar. Buttons (224) arranged on sidewall (218) are selectively operable, for example by squeezing, to actuate tabs (222) radially and thereby release tabs (222) from the trocar slots so obturator (210) may be separated from the trocar.

As shown in FIG. 8A, obturator (210) includes suture guide features in the form of a pair of needle entrance ports (226) arranged on obturator head (212), a pair of needle exit ports (228) arranged on a proximal portion of shaft (214), and a pair of deployable needle guide arms (230) arranged distally of needle exit ports (228) on shaft (214). Each needle entrance port (226) cooperates with a needle exit port (228) arranged on an opposing side of obturator (210) to guide a suture passer needle along a respective suture path extending obliquely relative to a central axis of obturator (210). As described below, a corresponding needle guide arm (230) guides a distal portion of a suture passer needle along the respective suture path.

Each needle entrance port (226) communicates with its respective needle exit port (228) via an internal pathway or interior (not shown) of obturator (210). In the present example, each needle entrance port (226) is defined by a needle guide tube (232) projecting angularly outwardly from head (212), and needle exit ports (228) are in the form of elongate slots. The elongate configuration of each needle exit port (228) enables the location at which a suture passer needle passes through needle exit port (228) to be adjusted proximally or distally to thereby alter the resulting suture path angle. In other examples, needle guide tubes (232) may be omitted from obturator (210), and/or needle exit ports (228) may be formed with various other shapes. In some examples, each needle entrance port (226) and/or its respective needle exit port (228) may include a sealing element, such as a pierceable seal, configured to maintain the corresponding suture path in a generally sealed state during use of obturator (210) as a wound closure device.

In the present example, needle entrance ports (226) are diametrically opposed relative to one another, and each needle entrance port (226) is diametrically opposed from a respective needle exit port (228) along an axially extending plane containing the obturator central axis. Accordingly, the first and second suture paths defined by needle ports (226, 228) of the present example lie in the same plane, and intersect to define an X-shaped pattern. In configurations in which the first and second suture paths define the same suture path angle, the sutures paths may intersect generally at the central axis of obturator (210). In other examples, needle entrance and exit ports (226, 228) may be arranged in various other configurations and quantities to define corresponding suture paths of various suture path angles.

As shown in FIGS. 8A and 8B, deployable needle guide arms (230) are coupled to obturator shaft (214) distally of needle exit ports (228), on a medial portion of shaft (214) in the present example. Needle guide arms (230) are diametrically opposed to one another in the same axial plane in which needle entrance and exit ports (226, 228) are arranged. Each needle guide arm (230) is configured to pivot about a proximal end (234) thereof between a deployed position (see FIG. 8A) and a retracted position (see FIG. 9D). In the retracted position, each needle guide arm (230) is received within a respective elongate recess (236) formed in a side of the medial portion of obturator shaft (214). Each recess (236) is formed with a depth sufficient to enable its guide arm (230) to lie flush with, or recessed slightly beneath, an outer surface of shaft (214) when guide arm (230) is retracted. Advantageously, this enables shaft (214) to pass freely through a working channel of a trocar when obturator (210) is coupled to the trocar. In the deployed position, each needle guide arm (230) extends radially outwardly from shaft (214) and generally perpendicular to the central axis of obturator (210), as shown in FIG. 8A. When in the deployed position, each needle guide arm (230) is configured to receive and guide the distal end of a suture passer needle, as well as anchor obturator (210) within a tissue opening, as described in greater detail below.

Needle guide arms (230) are selectively movable between their retracted and deployed positions by an actuator element (not shown), which may be arranged on obturator head (212), for example. Persons of ordinary skill in the art will recognize that the actuator element may be in the form of a button, switch, knob, wheel, or any other suitable element operatively coupled with needle guide arms (230) and movable between two or more positions to effect deployment and retraction of needle guide arms (230) relative to shaft (214). Additionally, the actuator element may be configured to maintain needle guide arms (230) at one or more intermediate positions between the retracted and deployed positions shown herein.

As shown in FIG. 8B, each needle guide arm (230) includes an elongate sealed aperture (238) configured to be pierced by a distal tip of a suture passer needle. An opening (240) extends from a lateral side of sealed aperture (238) to a corresponding lateral side of needle guide arm (230). Opening (240) is configured to allow a suture thread directed through sealed aperture (238) to be released laterally from needle guide arm (230), for example by applying a lateral pulling force to the suture thread. The elongate configuration of each sealed aperture (238) enables it to receive therethrough a suture passer needle oriented at various suture path angles relative to the central axis of obturator (210).

While obturator (210) of the present example includes distal needle guide structures in the form of pivoting needle guide arms (230), other variations of obturator (210) may include distal needle guide structures of various other forms configured to project radially outwardly from shaft (214) and guide distal portions of suture passer needles along first and second suture paths extending through obturator (210). Additionally, while obturator (210) of the present example is shown having suture guide features defining first and second suture paths, in other examples obturator (210) may have suture guide features arranged in various configurations to define a single suture path or three or more suture paths.

B. Exemplary Wound Closure Procedure Using Obturator Wound Closure Device Having Deployable Needle Guide Arms FIGS. 9A-9E show steps of an exemplary procedure for suturing closed a tissue opening (172) formed in tissue (170) by a trocar (not shown), such as trocar (102), using obturator (210) as wound closure device. Following completion of one or more surgical procedures using the trocar, the trocar is removed from tissue opening (172) and obturator shaft (214) is inserted distally through tissue opening (172), with needle guide arms (230) in their retracted positions. Once obturator (210) is positioned such that its head (212) generally confronts skin (174), needle guide arms (230) are deployed so that they confront a distal surface of tissue fascia (178), as shown in FIG. 9A. In that regard, pivoting proximal ends (234) of needle guide arms (230) are spaced distally from obturator head (212) by a distance generally corresponding to the anticipated thickness of tissue (170). Such a configuration enables needle guide arms (230) to abut a distal surface of a lower-most layer of fascia (178) when deployed, and thereby function as anchor elements configured to limit axial movement of obturator (210) relative to tissue (170) during a suturing procedure.

As shown in FIG. 9A, a suture passer needle (242) and a thread end (246) of a suture thread (244) are directed distally through obturator (210) along a first oblique suture path extending through a first needle entrance port (226), an opposed first needle exit port (228), an adjacent first portion of tissue fascia (178), and a corresponding first needle guide arm (230) via its sealed aperture (238), into body cavity (180). Suture passer needle (242) is then manipulated to release thread end (246) within body cavity (180), and is withdrawn proximally along first suture path.

As shown in FIG. 9B, suture passer needle (242) is then directed distally along a second oblique suture path extending through a second needle entrance port (226), an opposed second needle exit port (228), an adjacent second portion of tissue fascia (178), and a corresponding second needle guide arm (230) via its sealed aperture (238), into body cavity (180). Suture passer needle (242) and/or obturator (210) are then manipulated as needed to recapture thread end (246) with suture passer needle (242). Suture passer needle (242) and thread end (246) are then withdrawn proximally along the second suture path, yielding the configuration shown in FIG. 9C. As shown in FIG. 9C, a first thread leg (248) of suture thread (244) extends along the first suture path and captures a first portion of tissue fascia (178), a second thread leg (250) extends along the second suture path and captures an opposed second portion of tissue fascia (178), and an anchoring loop (252) extends between first and second thread legs (248, 250) within body cavity (180).

As shown in FIG. 9D, needle guide arms (230) are moved to their retracted positions to capture anchoring loop (252) of suture thread (244) between guide arms (230), and obturator (210) is withdrawn proximally from tissue opening (240). This enables first and second thread legs (248, 250) to slide distally through needle ports (226, 228) and release from obturator (210). As shown in FIG. 9E, needle guide arms (230) are then moved back to their deployed positions to facilitate release of anchoring loop (252) from guide arms (230) through lateral openings (240) (see FIG. 8B), thereby completely freeing suture thread (244) from obturator (210). Thread legs (248, 250) may then be pulled tight to draw together the captured portions of fascia (178) on either side of tissue opening (172), and then tied to form a suture knot (254) at a location just proximally of fascia (178), as shown in FIG. 9E. Optionally, the remaining portions of thread legs (248, 250) may be directed through fat (176) and skin (174) using suture needles, for example as shown in FIG. 4D, to create an additional "superficial" suture knot to fully close tissue opening (172) and promote optimal healing.

IV. EXEMPLARY OBTURATOR WOUND CLOSURE DEVICE HAVING DEPLOYABLE ANCHOR FEET

A. Exemplary Obturator Wound Closure Device

Figure 10:
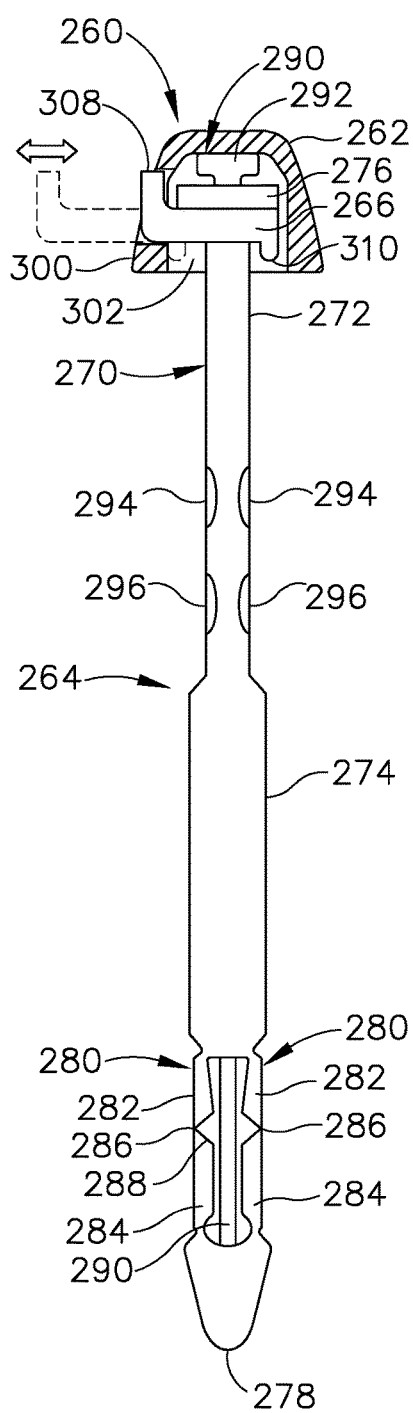
FIG. 10 depicts a side partial-sectional view of another exemplary trocar obturator configured for use as a wound closure device, having a shaft assembly and a head releasably coupled to the shaft assembly.
Figure 11A:
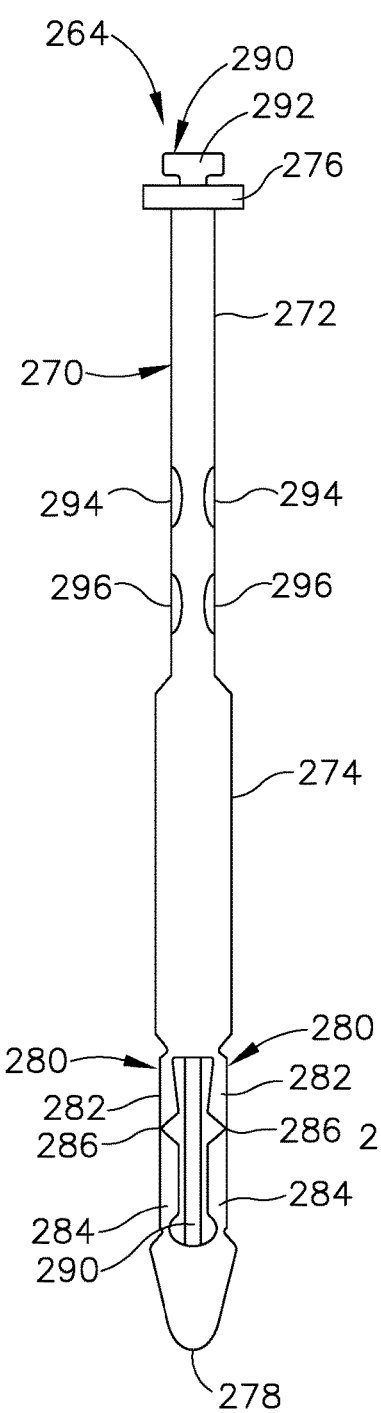
FIG. 11A depicts a side elevational view of the obturator shaft assembly of FIG. 10, showing a plunger in a distal position and anchor feet members in corresponding retracted positions.
Figure 11B:
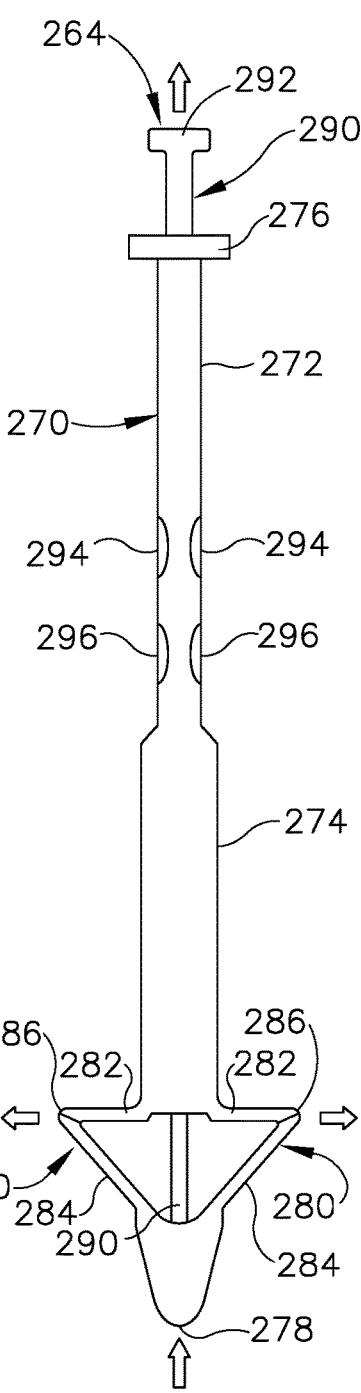
FIG. 11B depicts a side elevational view of the obturator shaft assembly of FIG. 11A, showing the plunger in a proximal position and anchor feet members in corresponding deployed positions.

FIGS. 10-11B show another exemplary obturator (260) configured for use as a wound closure device as well as a trocar insertion device. In the present example, obturator (260) is provided with suture guide features that enable obturator (260) to function as a wound closure device in combination with a trocar, such as trocar (102) as described below in connection with FIGS. 12A-12E. Obturator (260) includes a head (262) and a shaft assembly (264) extending distally from head (262) along a central axis. Head (262) includes a movable latch (266) configured to releasably couple head (262) with shaft assembly (264). Shaft assembly (264) includes a shaft (270) having a proximal shaft portion (272), a distal shaft portion (274), and a flange (276) arranged at a proximal end of proximal shaft portion (272). In the present example, distal shaft portion (274) is formed with a larger diameter than proximal shaft portion (272). Shaft assembly (264) terminates at a distal tip (278) configured to puncture tissue during a trocar insertion procedure.

Distal tip (278) is operatively coupled with distal shaft portion (274) by a pair of deployable anchor feet (280) extending therebetween. In the present example, each anchor foot (280) includes a proximal link (282), a distal link (284), and medial joint (286) hingedly coupling links (282, 284) to one another. Proximal links (282) are hingedly coupled to a distal end of distal shaft portion (274), and distal links (284) are hingedly coupled to a proximal end of distal tip (278). Anchor feet (280) are movable together between a retracted position (see FIGS. 10 and 11A) in which anchor feet links (282, 284) extend axially and generally flush with outer surfaces of distal shaft portion (274) and distal tip (278), and a deployed position (see FIG. 11B) in which anchor feet links (282, 284) project radially outwardly from distal shaft portion (274) and distal tip (278). Each anchor foot link (282, 284) includes a chamfered end (288) adjacent to medial joint (286). Chamfered ends (288) better enable proximal and distal links (282, 284) to hinge relative to one another when moving toward the deployed position, and are configured to contact one another in the deployed position to provide enhanced structural support to anchor feet links (282, 284) when deployed.

Shaft assembly (264) of obturator (260) further includes a plunger (290) slidably arranged within a central lumen of shaft (270). A proximal end of plunger (290) extends proximally of proximal shaft portion (272) and includes an actuation knob (292). A distal end of plunger (290) extends distally of distal shaft portion (274), through a gap defined between anchor feet (280), and couples to distal tip (278). Plunger (290) is slidable within the shaft lumen between a distal position in which anchor feet (280) are retracted, as shown in FIGS. 10 and 11A, and a proximal position in which anchor feet (280) are deployed, as shown in FIG. 11B. When plunger (290) is arranged in its distal position, its distal end pushes distal tip (278) axially away from distal shaft portion (274), thereby drawing anchor feet (280) radially inwardly toward plunger (290). When plunger (290) is arranged in its proximal position, its distal end pulls distal tip (278) axially toward distal shaft portion (274), thereby causing anchor feet (280) to expand radially outwardly away from plunger (290). In the present example, proximal movement of plunger (290) causes anchor feet (280) to deploy to a triangular configuration in which proximal links (282) extend perpendicularly relative to the obturator central axis and distal links (284) extend obliquely relative to the central axis. In various examples, plunger (290) may be resiliently biased toward one of its proximal or distal positions.

Shaft assembly (264) further includes suture guide features in the form of a pair of needle entrance ports (294) and a pair of needle exit ports (296) arranged distally of needle entrance ports (294). In the present example, needle entrance and exit ports (294, 296) are arranged on proximal shaft portion (272). Additionally, needle entrance ports (294) are diametrically opposed from one another, needle exit ports (296) are diametrically opposed from one another, and needle ports (294, 296) are arranged in a single axially extending plane containing the obturator central axis. Each needle entrance port (294) communicates with a respective needle exit port (296) arranged on an opposing side of obturator shaft (270), via an internal pathway (not shown) or interior of shaft (270), to define a respective suture path extending through obturator (260) at an oblique angle relative to the obturator central axis. In the present example, the suture path angles defined by the suture paths relative to the central axis are equal to one another. In other examples, needle entrance and exit ports (294, 296) may be arranged in various other quantities and configurations to define corresponding suture paths of various quantities, arrangements, and suture path angles. In some examples, each needle entrance port (294) and/or its respective needle exit port (296) may include a sealing element, such as a pierceable seal, configured to maintain the corresponding suture path in a generally sealed state during use of obturator (260) as a wound closure device.

Figures 12A, 12B, 12C:
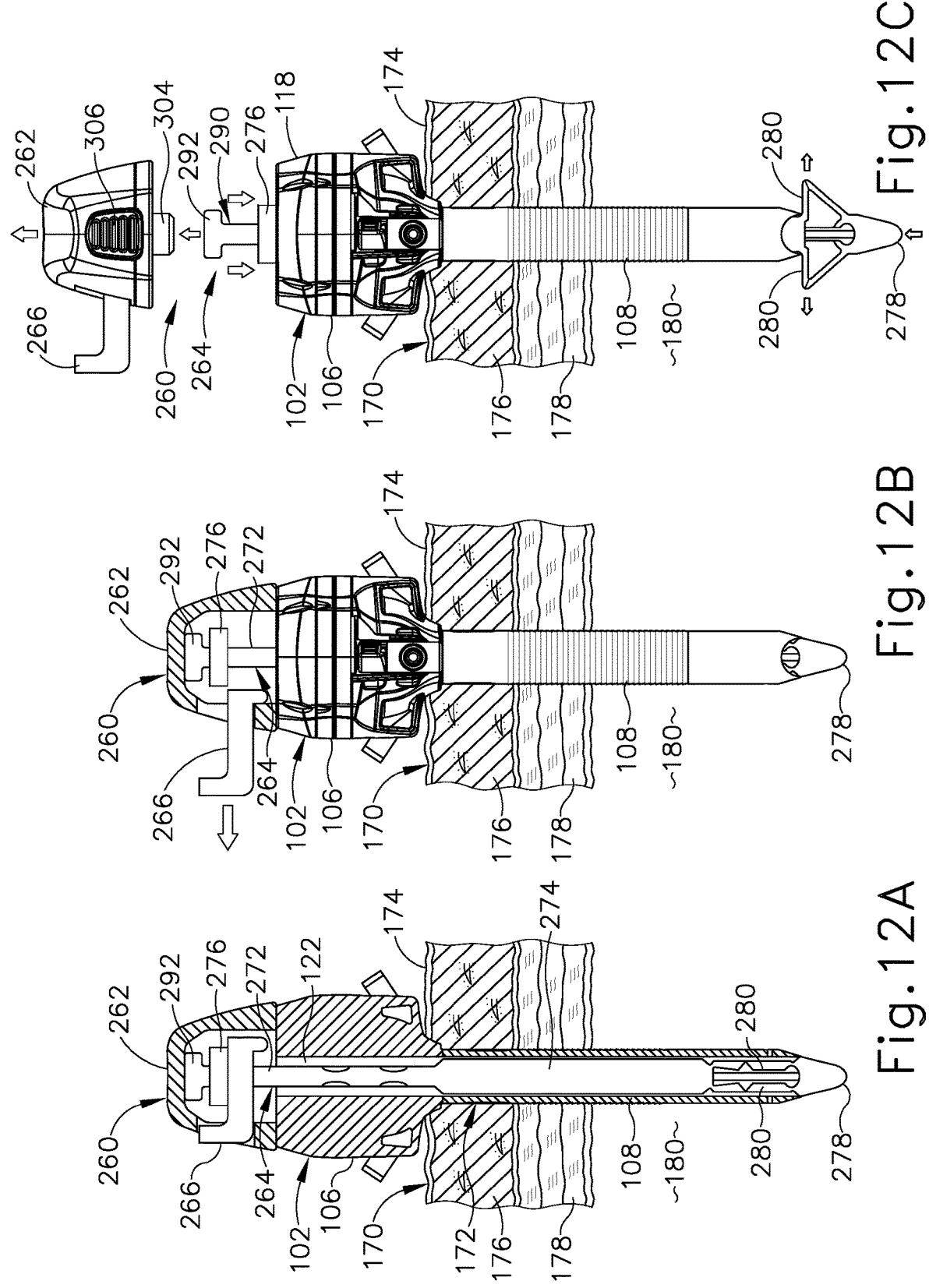
FIG. 12A depicts a schematic side sectional view of a trocar assembly including the obturator of FIG. 10 coupled with a trocar, showing the trocar assembly positioned within a tissue opening.
FIG. 12B depicts a schematic side sectional view of the trocar assembly and tissue of FIG. 12A, showing movement of a latch of the obturator head to an unlatched position.
FIG. 12C depicts a schematic side sectional view of the trocar assembly and tissue of FIG. 12B, showing removal of the obturator head from the obturator shaft assembly, and simultaneous distal movement of the shaft assembly within the trocar and proximal actuation of a plunger to deploy anchor feet members.

As shown best in FIG. 10, obturator head (262) is releasably coupled to proximal shaft portion (272) and is configured to selectively decouple from proximal shaft portion (272) during use. Head (262) includes a proximally tapering sidewall (300) defining an interior cavity (302). Interior cavity (302) is configured to receive a proximal end of the shaft assembly (264), including a proximal end of proximal shaft portion (272), shaft flange (276), and plunger knob (292). As shown in FIG. 12C, head (262) may include a pair of downwardly depending tabs (304) configured to releasably engage slots formed on a trocar, such as slots (134) of trocar (102), to thereby releasably couple obturator (260) with trocar (102). Buttons (306) on head (262) are operable to actuate tabs (304) to selectively release obturator head (262) from trocar (102), for example after a trocar insertion procedure.

As shown in FIG. 10, latch (266) of obturator head (262) is operable to translate between an inward latched position and an outward unlatched position. In the inward latched position, latch (266) engages an underside of shaft flange (276) to thereby secure head (262) to shaft assembly (264), as well as restrain plunger (290) in its distal position to maintain anchor feet (280) in their retracted position. In configurations in which plunger (290) is resiliently biased proximally, latch (266) is configured to overcome the bias force and compress plunger knob (292) toward flange (276) to maintain plunger (290) in its distal position. In the outward unlatched position, latch (266) releases shaft flange (276) to thereby enable head (262) to be separated from shaft assembly (264). In the present example, latch (266) includes a first projection (308) arranged at an outward end thereof to facilitate manual actuation of latch (266), and a second projection (310) arranged at an inward end thereof to prevent latch (266) from decoupling from head (262) when in its outward unlatched position. Those of ordinary skill in the art will recognize that latch (266) make take various alternative forms in other variations of obturator (260).

B. Exemplary Wound Closure Procedure Using Obturator Wound Closure Device Having Deployable Anchor Feet FIGS. 12A-12F show steps of an exemplary procedure for suturing closed a tissue opening (172) formed in tissue (170) by trocar (102), using obturator (260) as a wound closure device. Following completion of one or more surgical procedures using trocar (102), all surgical instruments are withdrawn from working channel (122) of trocar (102). Obturator (260) is manipulated by a surgeon, with latch (266) in its latched position, to insert shaft assembly (264) distally through working channel (122). In this state, as shown in FIG. 12A, proximal shaft portion (272) of obturator (260) resides within trocar housing assembly (106), distal shaft portion (274) resides within trocar cannula (108), and distal tip (278) projects through the distal opening of cannula (108) into body cavity (180). Additionally, anchor feet (280) remain in their retracted positions.

As indicated by directional arrows shown in FIGS. 12B and 12C, latch (266) is moved to its outward unlatched position to enable proximal separation of obturator head (262) from obturator shaft assembly (264) and thereby expose plunger knob (292). Additionally, head buttons (306) are actuated to decouple head tabs (304) from proximal housing head (118) of trocar (102). As shown in FIG. 12C, shaft assembly (264) is advanced distally until shaft flange (276) abuts proximal housing head (118) of trocar (102). In that regard, flange (276) is formed with a diameter larger than the diameter of a proximal opening to trocar working channel (122) formed in proximal housing head (118). Accordingly, flange (276) abuts proximal housing head (118) to thereby limit distal axial movement of obturator shaft assembly (264) relative to trocar (102). In this position, anchor feet (280) clear the distal end of trocar cannula (108), and the oblique suture paths defined by obturator (260) align with the oblique suture paths defined by trocar (102), described above. Plunger (290) is then moved to its proximal position to deploy anchor feet (280). Plunger (290) may be actuated either manually or automatically by a bias force exerted by a resilient member (not shown). Once deployed, anchor feet (280) are configured to abut the distal end of cannula (108) to thereby restrict proximal axial movement of obturator shaft assembly (264) relative to trocar (102). In this configuration, trocar (102) and obturator (260) are configured to be used in combination to guide placement of a suture thread in tissue (170), as described below.

Figure 12F:
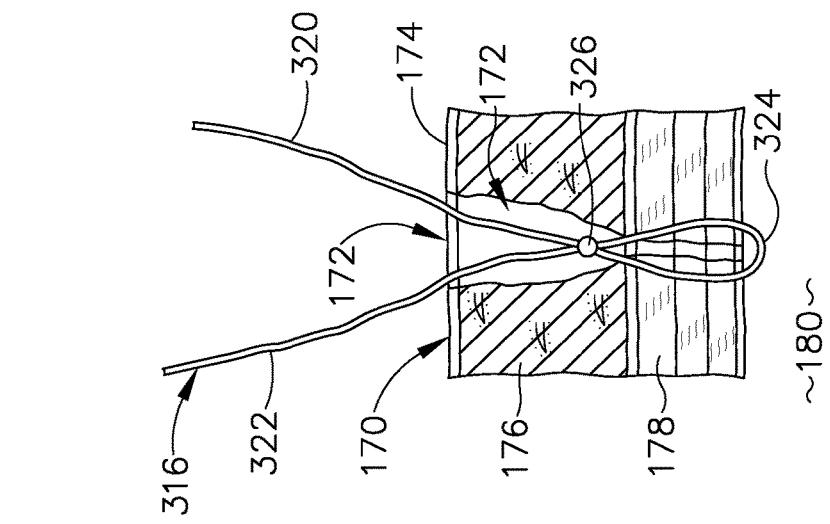
FIG. 12F depicts a schematic side sectional view of the suture thread and tissue of FIG. 12E, showing formation of a suture knot that closes a distal portion of the tissue opening.
Figure 12E:
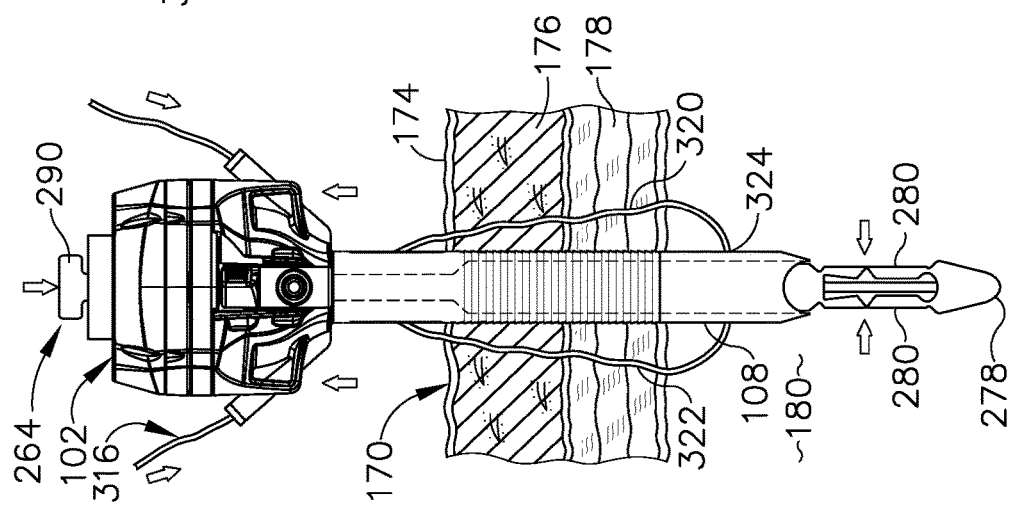
FIG. 12E depicts a schematic side sectional view the trocar assembly and tissue of FIG. 12D, showing distal actuation of the plunger to retract the anchor feet members and proximal withdrawal of the trocar assembly from the tissue opening.
Figure 12D:
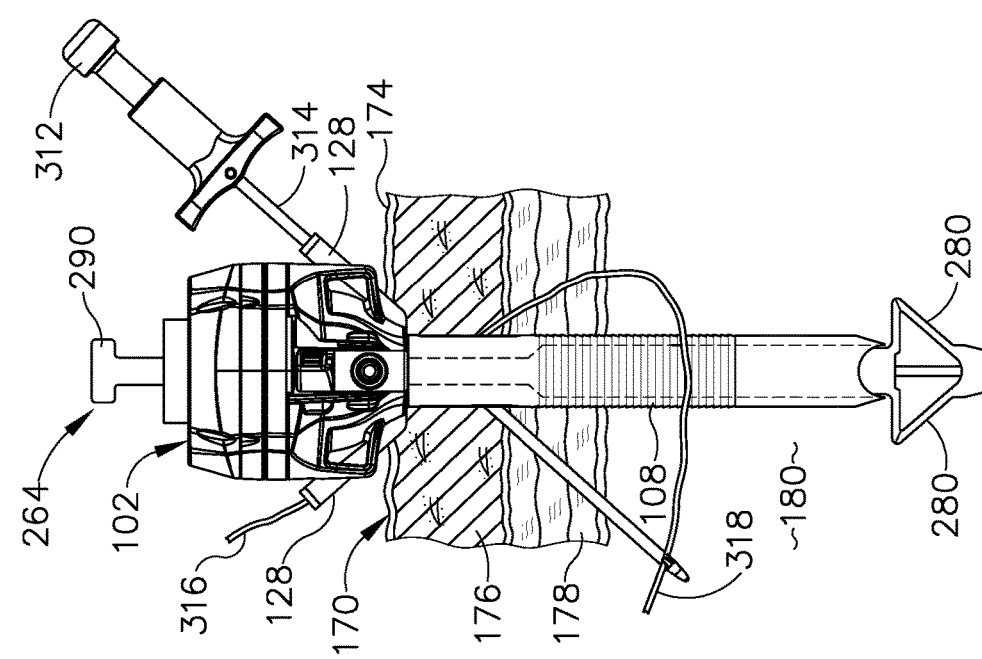
FIG. 12D depicts a schematic side sectional view the trocar assembly and tissue of FIG. 12C following insertion of a suture passer needle and suture thread end distally through the trocar assembly and tissue fascia along a first oblique suture path, showing insertion of the suture passer needle distally through the trocar assembly and tissue fascia along a second oblique suture path to capture the suture thread end.

As shown in FIG. 12D, a suture passer needle (314) of a suture passer device (312) has been manipulated by an operator to direct a thread end (318) of a suture thread (316) distally along a first suture path extending through a first needle guide tube (128) of trocar (102), a first needle entrance port (294) of obturator (260), an opposed first needle exit port (296) of obturator (260), a corresponding first needle exit port (129) of trocar (102), and an adjacent first portion of tissue fascia (178), into body cavity (180). Thread end (318) was then released by suture passer needle (314) within body cavity (180). As shown in FIG. 12D, suture passer needle (314) is now directed distally along a second suture path extending through a second needle guide tube (128) of trocar (102), a second needle entrance port (294) of obturator (260), an opposed second needle exit port (296) of obturator (260), a corresponding second needle exit port (129) of trocar (102), and an adjacent second portion of tissue fascia (178), into body cavity (180). Suture passer needle (314) and/or trocar (102) and obturator (260) are manipulated as needed to recapture suture thread end (318) with suture passer needle (314). Suture passer needle (314) and thread end (318) are then withdrawn proximally along the second suture path, yielding the suture thread configuration shown in FIG. 12E. In particular, a first thread leg (320) of suture thread (316) extends along the first suture path to capture a first portion of fascia (178), a second thread leg (322) of suture thread (316) extends along the second suture path to capture an opposed second portion of fascia (178), and an anchoring loop (324) extends between first and second thread legs (320, 322) within body cavity (180).

As indicated by directional arrows shown in FIG. 12E, plunger (290) is actuated distally to thereby retract anchor feet (280) inwardly. Trocar (102) and obturator shaft assembly (264) are then withdrawn distally together from tissue opening (172), thereby releasing suture thread legs (320, 322) from trocar (102) and obturator (260). Thread legs (320, 322) may then be pulled tight to draw together the captured portions of fascia (178) on either side of tissue opening (172), and then tied to form a suture knot (326) at a location just proximally of fascia (178), as shown in FIG. 12F. Optionally, the remaining portions of thread legs (320, 322) may be directed through fat (176) and skin (174) using suture needles, for example as shown in FIG. 4D, to create an additional "superficial" suture knot to fully close tissue opening (172) and promote optimal healing. Though not shown, it will be appreciated that in some variations of the exemplary wound closure procedure described above, obturator (260) may be employed as a wound closure device independently of trocar (102).

V. Alternative Exemplary Obturator Wound Closure Device Having Deployable Anchor Feet A. Exemplary Obturator Wound Closure Device FIGS. 13-14B show another exemplary obturator (330) configured for use as a wound closure device as well as a trocar insertion device. Obturator (330) is provided with suture guide features that enable obturator (330) to function as a wound closure device independently of a trocar. In that regard, obturator (330) is generally similar to obturator (260) described above, except as otherwise described below. Similar to obturator (260), obturator (330) includes a head (332) and a shaft assembly (334) extending distally from head (332) along a central axis. Head (332) includes a movable latch (336) configured to releasably couple head (332) with shaft assembly (334). Shaft assembly (334) includes a shaft (338) having a proximal shaft portion (340), a distal shaft portion (342), and a flange (344) arranged at a proximal end of proximal shaft portion (340). Shaft assembly (334) terminates at a distal tip (346) configured to puncture tissue during a trocar insertion procedure. As described below, the components of shaft assembly (334), including flange (344), are formed with diameters smaller than the diameter of the working channel of the trocar with which obturator (330) is used.

Distal tip (346) is operatively coupled with distal shaft portion (342) by a pair of deployable anchor feet (348) extending therebetween. Anchor feet (348) are similar to anchor feet (348) described above in that each anchor foot (348) includes a proximal link (350), a distal link (352), and medial joint (354) hingedly coupling links (352, 354) to one another. Proximal links (352) are hingedly coupled to a distal end of distal shaft portion (342), and distal links (354) are hingedly coupled to a proximal end of distal tip (346). Anchor feet (348) are movable together between a retracted position (see FIGS. 13 and 14A) in which anchor feet links (352, 354) are angled and biased inwardly towards the central axis of shaft assembly (334), and a deployed position (see FIG. 14B) in which anchor feet links (352, 354) project radially outwardly from distal shaft portion (342) and distal tip (346). As shown best in FIG. 14B, anchor feet links (352, 354) may include chamfered ends adjacent to medial joint (354) configured to contact one another in the deployed position to provide mutual structural support to anchor feet links (352, 354) in the deployed position.

Shaft assembly (334) of obturator (330) further includes a plunger (356) slidably arranged within a central lumen of shaft (338). Plunger (356) includes a proximal knob (358) and is functionally similar to plunger (290) described above in that plunger (356) is movable between proximal and distal positions for deploying and retracting anchor feet (348). In various examples, plunger (356) may be resiliently biased toward one of its proximal or distal positions.

Shaft assembly (334) further includes suture guide features in the form of a pair of needle entrance ports (360) and a pair of needle exit ports (362) arranged distally of needle entrance ports (360). In the present example, needle entrance and exit ports (360, 362) are arranged on distal shaft portion (342). Additionally, needle entrance ports (360) are diametrically opposed from one another, needle exit ports (362) are diametrically opposed from one another, and needle ports (294, 296) are arranged in a single axially extending plane containing the obturator central axis. Each needle entrance port (360) communicates with a respective needle exit port (362) arranged on an opposed side of obturator shaft (338) to define a respective suture path extending through obturator (330) at an oblique angle relative to the obturator central axis. In the present example, the suture path angles defined by the suture paths relative to the central axis are equal to one another. In other examples, needle entrance and exit ports (360, 362) may be arranged in various other quantities and configurations to define corresponding suture paths of various quantities, arrangements, and suture path angles. In some examples, each needle entrance port (360) and/or its respective needle exit port (362) may include a sealing element, such as a pierceable seal, configured to maintain the corresponding suture path in a generally sealed state during use of obturator (330) as a wound closure device.

Similar to head (262) of obturator (260), head (332) of obturator (330) is releasably coupled to proximal shaft portion (340) of obturator shaft assembly (334), and is configured to selectively decouple from proximal shaft portion (340) during use. Head (332) includes a proximally tapering sidewall (364) defining an interior cavity (366). As shown in FIG. 13, interior cavity (366) is configured to receive a proximal end of the shaft assembly (334), including a proximal end of proximal shaft portion (340), shaft flange (344), and plunger knob (358). As shown in FIG. 15C, head (332) may include a pair of downwardly depending tabs (368) configured to releasably engage slots formed on a trocar, such as slots (134) of trocar (102), to thereby releasably couple obturator (330) with trocar (380). Buttons (370) on head (332) are operable to actuate tabs (368) to selectively separate obturator head (332) from trocar (380), for example after a trocar insertion procedure.

Similar to latch (266) of obturator (260), latch (336) of obturator (330) is movable between latched position and unlatched positions to selectively couple and decouple obturator head (332) with obturator shaft assembly (334). As shown in FIG. 13, latch (336) is pivotally coupled to head (332) at a pivot joint (372) and is configured to pivot relative to head (332) between the latched and unlatched positions. In the present example, latch (336) is generally L-shaped and includes a first latch leg (374) having a user engagement feature, and a second latch leg (376) having a shaft engagement feature.

In the latched position, shown in FIGS. 13 and 14A, second latch leg (376) extends generally perpendicularly to shaft (338) to engage proximal shaft portion (340) and thereby secure head (332) to shaft assembly (334), as well as restrain plunger (356) in its distal position to maintain anchor feet (348) in their retracted position. When moved to the latched position, second latch leg (376) may be received within a groove or recess (not shown) formed on proximal shaft portion (340), or otherwise frictionally engage proximal shaft portion (340). In the unlatched position, shown in FIGS. 13 and 14B, second latch leg (376) is angled obliquely relative to shaft (338) to thereby disengage proximal shaft portion (340) and permit separation of head (332) from shaft assembly (334).

B. Exemplary Wound Closure Procedure Using Alternative Obturator Wound Closure Device Having Deployable Anchor Feet FIGS. 15A-15F show steps of an exemplary procedure for suturing closed a tissue opening (172) formed in tissue (170) by a trocar (380), using obturator (330) as a wound closure device independently from a trocar (380). Trocar (380) is generally similar in structure to trocar (102) described above, as indicated by like reference numerals. Because obturator (330) is employed as a wound closure device independently of trocar (380) in the present example, suture guide features are omitted from trocar (380). It will be understood, however, that in some variations obturator (330) may be used in combination with a trocar that includes suture guide features, such as trocar (102). Following completion of one or more surgical procedures using trocar (380), all surgical instruments are withdrawn from working channel (122) of trocar (380). Obturator (330) is manipulated by a surgeon, with latch (336) in its latched position, to insert shaft assembly (334) distally through working channel (122). In this state, as shown in FIG. 15A, proximal shaft portion (340) of obturator (330) resides within trocar housing assembly (106), distal shaft portion (342) resides within trocar cannula (108), and distal tip (346) extends through the distal opening of cannula (108). Additionally, anchor feet (348) remain in their retracted position.

As indicated by directional arrows shown in FIGS. 15B and 15C, latch (336) is pivoted to its unlatched position to enable proximal separation of obturator head (332) from obturator shaft assembly (334) and thereby expose plunger knob (358).

Additionally, head buttons (370) are actuated to decouple head tabs (368) from proximal housing head (118) of trocar (380). As shown in FIG. 15C, trocar (380) is raised proximally while shaft assembly (334) is pushed distally through trocar (380) so anchor feet (348) clear the distal end of trocar cannula (108).

As shown in FIG. 15D, plunger (290) is moved to its proximal position to deploy anchor feet (280) radially outwardly. Plunger (290) may be actuated either manually, or automatically by a bias force exerted by a resilient member (not shown), for example. Once deployed, anchor feet (280) are configured to abut a distal surface of tissue fascia (178) and thereby restrict proximal movement of obturator shaft assembly (334) relative to tissue (170). Consequently, trocar (380) may be withdrawn proximally from tissue opening (172) while obturator shaft assembly (334) remains, as shown in FIG. 15E. As described above, and as shown in FIG. 15E, obturator shaft flange (344) is formed with a diameter smaller than that of working channel (122) of trocar (380), thereby enabling obturator shaft assembly (334) to pass distally through working channel (122).

As shown in FIG. 15F, trocar (380) has been fully removed leaving only obturator shaft assembly (334) within tissue opening (172). A suture passer needle (382) and suture thread (384) is then directed through obturator shaft assembly (334) and tissue fascia (178) along first and second oblique suture paths defined by respective pairs of needle entrance and exit ports (360, 362), to thereby capture first and second portions of fascia (178). Once suture thread (384) has been fully threaded through fascia (178), plunger (356) is actuated distally to retract anchor feet (348), similar to the step shown in FIG. 12E in connection with the wound closure procedure described above. Obturator shaft assembly (334) is then withdrawn proximally from tissue opening (172), thereby releasing suture thread (384) from shaft assembly (334). As described above in connection with other wound closure methods described herein, suture thread (384) is then manipulated to form a suture knot securing together the first and second captured portions of fascia (178). Optionally, a second, "superficial" knot may be formed proximally of the first knot to secure together fat (176) and skin (174) and promote optimal healing of tissue opening (172).

The teachings presented herein may be further combined with various teachings of any one or more of the following: U.S. App. Ser. No. 15/637,690, entitled "Needle Guide Instrument with Traverse Suture Capture Feature," filed on Jun. 29, 2017, issued as U.S. Pat. No. 10,675,018 on Jun. 9, 2020, the disclosure of which is incorporated by reference herein; U.S. App. Ser. No., 15/637,702, entitled "Suture Grasping Instrument," filed on Jun. 29, 2017, issued as U.S. Pat. No. 10,639,029 on May 5, 2020, the disclosure of which is incorporated by reference herein; U.S. App. Ser. No. 15/637,683, incorporated by reference above, issued as U.S. Pat. No. 10,639,068 on May 5, 2020; U.S. App. Ser. No. 15/637,688, incorporated by reference above, issued as U.S. Pat. No. 10,485,580 on Nov. 26, 2019; U.S. App. Ser. No. 15/637,712, entitled "Suture Passing Instrument with Puncture Site Identification Feature," filed on Jun. 29, 2017, issued as U.S. Pat. No. 10,709,440 on Jul. 14, 2020, the disclosure of which is incorporated by reference herein; U.S. App. Ser. No., 15/637,707, entitled "Surgical Port with Wound Closure Channels," filed on Jun. 29, 2017, issued as U.S. Pat. No. 10,568,649 on Feb. 25, 2020, the disclosure of which is incorporated by reference herein; U.S. App. Ser. No. 15/637,735, entitled "Trocar Obturator with Detachable Rotary Tissue Fastener," filed on jun. 29, 2017, issued as U.S. Pat. No. 10,709,473 on Jul. 14, 2020, the disclosure of which is incorporated by reference herein; U.S. App. Ser. No. 15/637,778, entitled "Method of Suturing a Trocar Patch Incision," filed on Jun. 29, 2017, published as U.S. Pub. No. 2019/0000496 on Jan. 3, 2019, the disclosure of which is incorporated by reference herein; and/or other patents and patent application publications incorporated by reference above.

VI. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An obturator configured for use with a trocar, the obturator comprising: (a) a head; (b) a shaft extending distally from the head along a central axis, wherein the shaft is configured to be received within a working channel of a trocar; (c) a distal tip configured to puncture tissue; (d) first and second needle entrance ports each arranged on at least one of the head or the shaft; and (e) first and second needle exit ports arranged on the shaft, wherein the first needle entrance port communicates with the first needle exit port to define a first suture path extending obliquely relative to the central axis, wherein the first suture path includes at least one first sealing element, wherein the second needle entrance port communicates with the second needle exit port to define a second suture path extending obliquely relative to the central axis, wherein the second suture path includes at least one second sealing element.

Example 2

The obturator of Example 1, wherein the first and second suture paths extend through a device interior of the wound closure device.

Example 3

The obturator of Example 2, wherein the head and the shaft collectively define the device interior, wherein each of the needle entrance ports and the needle exit ports opens to the device interior.

Example 4

The obturator of any one or more of the preceding Examples, wherein the first and second needle entrance ports are arranged on respective first and second side portions of the head.

Example 5

The obturator of any one or more of the preceding Examples, wherein the first and second needle entrance ports comprise first and second elongate slots.

Example 6

The obturator of any one or more of the preceding Examples, wherein the first and second needle exit ports comprise first and second elongate slots.

Example 7

The obturator of any one or more of the preceding Examples, further comprising third and fourth needle exit ports arranged on the cannula distally of the first and second needle exit ports.

Example 8

The obturator of Example 7, wherein the third and fourth needle exit ports are aligned axially with the first and second needle exit ports.

Example 9

The obturator of Example 1, further comprising at least one needle guide member arranged on the shaft distally of the first and second needle exit ports, wherein the at least one needle guide member is configured to guide a distal end of a suture passer needle directed along at least one of the first or second suture paths.

Example 10

The obturator of Example 9, wherein the at least one needle guide member comprises a pair of needle guide members, wherein each needle guide member is movable relative to the cannula between a retracted position and a deployed position in which the at least one needle guide member projects radially outwardly from the shaft.

Example 11

The obturator of any one or more of the preceding Examples, further comprising at least one anchor member arranged at a distal end portion of the shaft, wherein the at least one anchor member is movable relative to the shaft between a retracted position and a deployed position in which the at least one anchor member projects radially outwardly from the shaft.

Example 12

The obturator of Example 11, further comprising a plunger slidably arranged within a central lumen of the shaft, wherein the plunger is operatively coupled with the at least one anchor member, wherein the plunger is slidable axially within the shaft between a first axial position for placing the at least one anchor member in the retracted position and a second axial position for placing the at least one anchor member in the deployed position.

Example 13

The obturator of Example 12, wherein a distal end of the plunger is coupled to the distal tip of the obturator, wherein the distal tip is movable with the plunger relative to the shaft between the first and second axial positions.

Example 14

The obturator of Example 12, wherein the plunger is resiliently biased toward one of the first position or the second position, wherein the head is selectively decouplable from the shaft, wherein the head is configured to overcome a bias force associated with the plunger to thereby maintain the plunger in one of the first axial position or the second axial position when the head is coupled with the shaft.

Example 15

The obturator of any one or more of the preceding Examples, wherein the needle entrance ports are arranged on the shaft.

Example 16

An obturator configured for use with a trocar, the obturator comprising: (a) a shaft extending along a central axis; (b) a head releasably coupled to a proximal end of the shaft; (c) a distal tip configured to puncture tissue; (d) a first pair of needle ports configured to direct a suture passer needle through the obturator along a first suture path oriented obliquely relative to the central axis; and (e) a second pair of needle ports configured to direct a suture passer needle through the obturator along a second suture path oriented obliquely relative to the central axis.

Example 17

The obturator of Example 16, wherein the head includes a latch, wherein the latch is movable between a first position in which the latch is configured to secure the head to the shaft, and a second position in which the latch is configured to permit the head to be separated from the shaft.

Example 18

The obturator of any one or more of Examples 16 through 17, wherein the obturator further includes at least one anchor member arranged at a distal end portion of the shaft, wherein the at least one anchor member is movable relative to the shaft between a retracted position and a deployed position in which the at least one anchor member projects radially outwardly from the shaft.

Example 19

A trocar assembly, comprising: (a) a trocar including: (i) a housing assembly, (ii) a cannula extending distally from the housing assembly, and (iii) a working channel extending axially through the housing assembly and the cannula; and (b) the obturator of claim 16, wherein a proximal end of the obturator is configured to pass distally through the working channel when the head is removed from the shaft.

Example 20

A wound closure device, comprising: (a) a head; (b) a shaft extending distally from the head along a central axis; (c) a deployable member coupled to the shaft, wherein the deployable member is movable between a retracted position in which the shaft is configured to be inserted into a working channel of a trocar, and a deployed position in which the deployable member projects radially outwardly from the shaft and is configured to abut an adjacent structure to limit axial movement of the wound closure device relative to the adjacent structure; (d) a first pair of needle ports configured to guide a suture passer needle along a first suture path extending through the wound closure device obliquely relative to the central axis; and (e) a second pair of needle ports configured to guide a suture passer needle along a second suture path extending through the wound closure device obliquely relative to the central axis.

VII. MISCELLANEOUS

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pat. No. 8,844,789, entitled "Automated End Effector Component Reloading System for Use with a Robotic System," issued Sep. 30, 2014, the disclosure of which is incorporated by reference herein; U.S. Pat. No. 8,820,605, entitled "Robotically-Controlled Surgical Instruments," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. Pub. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An obturator configured for use with a trocar, the obturator comprising:
   (a) a head, wherein the head includes a latch;
   (b) a shaft extending distally from the head along a central axis, wherein the shaft is configured to be received within a working channel of a trocar, wherein the latch of the head is movable between a first position in which the latch is configured to secure the head to the shaft, and a second position in which the latch is configured to permit the head to be separated from the shaft;
   (c) a distal tip configured to puncture tissue;
   (d) first and second needle entrance ports each arranged on at least one of the head or the shaft;
   (e) first and second needle exit ports arranged on the shaft; and
   (f) at least one anchor member arranged on a distal portion of the shaft, wherein the at least one anchor member is selectively actuatable relative to the shaft between a retracted position and a deployed position, wherein in the deployed position the at least one anchor member projects radially outwardly from the shaft,
   wherein the first needle entrance port communicates with the first needle exit port to define a first suture path extending obliquely relative to the central axis,
   wherein the second needle entrance port communicates with the second needle exit port to define a second suture path extending obliquely relative to the central axis.

2. The obturator of claim 1, wherein the first and second suture paths extend through a device interior of the obturator.

3. The obturator of claim 2, wherein the head and the shaft collectively define the device interior, wherein each of the needle entrance ports and the needle exit ports opens to the device interior.

4. The obturator of claim 1, wherein the first and second needle entrance ports are arranged on respective first and second side portions of the head.

5. The obturator of claim 1, wherein the first and second needle entrance ports comprise first and second elongate slots.

6. The obturator of claim 1, wherein the first and second needle exit ports comprise first and second elongate slots.

7. The obturator of claim 1, further comprising third and fourth needle exit ports arranged on the shaft distally of the first and second needle exit ports.

8. The obturator of claim 1, further comprising at least one needle guide member arranged on the shaft distally of the first and second needle exit ports, wherein the at least one needle guide member is configured to guide a distal end of a suture passer needle directed along at least one of the first or second suture paths.

9. The obturator of claim 8, wherein the at least one needle guide member comprises a pair of needle guide members, wherein each needle guide member is movable relative to the shaft between a retracted position and a deployed position in which the at least one needle guide member projects radially outwardly from the shaft.

10. The obturator of claim 1, further comprising a plunger slidably arranged within a central lumen of the shaft, wherein the plunger is operatively coupled with the at least one anchor member, wherein the plunger is slidable axially within the shaft between a first axial position for placing the at least one anchor member in the retracted position and a second axial position for placing the at least one anchor member in the deployed position.

11. The obturator of claim 10, wherein a distal end of the plunger is coupled to the distal tip of the obturator, wherein the distal tip is movable with the plunger relative to the shaft between the first and second axial positions.

12. The obturator of claim 10, wherein the plunger is resiliently biased toward one of the first axial position or the second axial position, wherein the head is selectively decouplable from the shaft, wherein the head is configured to overcome a bias force associated with the plunger to thereby maintain the plunger in one of the first axial position or the second axial position when the head is coupled with the shaft.

13. The obturator of claim 1, wherein the needle entrance ports are arranged on the shaft.

14. The obturator of claim 1, wherein the shaft includes a proximal shaft portion and a distal shaft portion, wherein the distal shaft portion is formed with a larger diameter than the proximal shaft portion.

15. The obturator of claim 1, wherein the distal tip is movable proximally and distally relative to the shaft between the retracted position and the deployed position.

16. The obturator of claim 15, wherein the distal tip is translatable relative to the shaft along the central axis thereof between the retracted position and the deployed position.

17. The obturator of claim 1, wherein the latch in the first position is configured to engage a proximal feature of the shaft to secure the head to the shaft, wherein the latch in the second position is configured to disengage the proximal feature to permit the head to be separated from the shaft.

18. A trocar assembly, comprising:
   (a) a trocar including:
      (i) a housing assembly,
      (ii) a cannula extending distally from the housing assembly, and
      (iii) a working channel extending axially through the housing assembly and the cannula; and
   (b) an obturator configured for use with the trocar, the obturator comprising:
      (i) a shaft extending along a central axis,
      (ii) a head releasably coupled to a proximal end of the shaft,
      (iii) a distal tip configured to puncture tissue,
      (iv) a first pair of needle ports configured to direct a suture passer needle through the obturator along a first suture path oriented obliquely relative to the central axis, and
      (v) a second pair of needle ports configured to direct a suture passer needle through the obturator along a second suture path oriented obliquely relative to the central axis,
   wherein the proximal end of the shaft is configured to pass distally through the working channel when the head is removed from the shaft.

19. A wound closure device, comprising:
   (a) a head;
   (b) a shaft extending distally from the head along a central axis, wherein the head is selectively decouplable from the shaft;
   (c) a plunger slidably arranged within a central lumen of the shaft, wherein the plunger is resiliently biased toward a proximal position;
   (d) a deployable member coupled to the shaft and the plunger, wherein the deployable member is actuatable by the plunger between a retracted position in which the shaft and the deployable member are configured to be inserted into a working channel of a trocar, and a deployed position in which the deployable member projects radially outwardly from the shaft and is configured to abut an adjacent structure to limit axial movement of the wound closure device relative to the adjacent structure, wherein the head is configured to overcome the resilient bias of the plunger to thereby maintain the plunger in a distal position and the deployable member in the retracted position when the head is coupled with the shaft and the plunger, wherein the plunger is configured to assume the proximal position and the deployable member is configured to assume the deployed position when the head is decoupled from the shaft and the plunger;
   (e) a first pair of needle ports configured to guide a suture passer needle along a first suture path extending through the wound closure device obliquely relative to the central axis; and
   (f) a second pair of needle ports configured to guide a suture passer needle along a second suture path extending through the wound closure device obliquely relative to the central axis.

20. The wound closure device of claim 19, wherein the head includes a latch, wherein the latch of the head is movable between a first position in which the latch is configured to secure the head to the shaft, and a second position in which the latch is configured to permit the head to be separated from the shaft.

* * * * *